(12) United States Patent
Mikami et al.

(10) Patent No.: US 10,667,772 B2
(45) Date of Patent: Jun. 2, 2020

(54) RADIATION-IRRADIATION DEVICE

(71) Applicant: FUJIFILM Corporation, Tokyo (JP)

(72) Inventors: Yuji Mikami, Kanagawa (JP);
Noriyuki Onobori, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 263 days.

(21) Appl. No.: 15/923,147

(22) Filed: Mar. 16, 2018

(65) Prior Publication Data

US 2018/0199900 A1 Jul. 19, 2018

Related U.S. Application Data

(63) Continuation of application No. PCT/JP2016/002484, filed on May 23, 2016.

(30) Foreign Application Priority Data

Sep. 29, 2015 (JP) .................................. 2015-192067
Nov. 24, 2015 (JP) .................................. 2015-228537

(51) Int. Cl.
*A61B 6/00* (2006.01)
*A61B 90/50* (2016.01)
*G01T 1/00* (2006.01)

(52) U.S. Cl.
CPC .......... *A61B 6/4405* (2013.01); *A61B 6/4429* (2013.01); *A61B 90/50* (2016.02);
(Continued)

(58) Field of Classification Search
CPC ....... A61B 6/4441; A61B 6/4405; A61B 6/54; A61B 6/542; A61B 6/4429; A61B 6/44;
(Continued)

(56) References Cited

U.S. PATENT DOCUMENTS 6,374,937 B1 * 4/2002 Galando ............. A61B 6/4405
180/19.1
6,609,826 B1 8/2003 Fujii et al.
(Continued)

FOREIGN PATENT DOCUMENTS

JP S38-18230 Y1 8/1963
JP S60-79423 U 6/1985
(Continued)

OTHER PUBLICATIONS

Communication dated Nov. 14, 2018, from the European Patent Office in counterpart European Application No. 16850535.2.
(Continued)

*Primary Examiner* — Don K Wong

(74) *Attorney, Agent, or Firm* — Sughrue Mion, PLLC

(57) ABSTRACT

There is provided a radiation-irradiation device of which a direction can be easily changed obliquely with a simple structure. A rear wheel unit (12R) of a radiation-irradiation device includes first locking means that includes a front operating portion (109F) of a brake pedal (109), a shaft (108), a gear (107), a cam (106), a rod (104), a lever (105), and a disc (103) and restrains the traveling rotation of a wheel (102). Further, the rear wheel unit (12R) includes second locking means that includes a rear operating portion (109R) of the brake pedal (109), the shaft (108), the gear (107), and the cam (106) and restrains the revolution of a casing (101).

12 Claims, 25 Drawing Sheets

(52) U.S. Cl.
CPC .............. *G01T 1/00* (2013.01); *A61B 6/4452* (2013.01); *A61B 6/4488* (2013.01); *A61B 6/46* (2013.01)

(58) Field of Classification Search
CPC ......... A61B 6/4476; A61B 6/467; G01T 1/00; B60K 7/00; B60K 17/358; B62K 2204/00; B62K 2201/00; B62D 61/06; B62D 61/10
See application file for complete search history.

(56) References Cited

U.S. PATENT DOCUMENTS

| | | | |
|---|---|---|---|
| 2003/0024340 A1 | 2/2003 | Tonnesland et al. | |
| 2012/0155616 A1 | 6/2012 | Rijken et al. | |
| 2012/0195405 A1 | 8/2012 | Woudstra et al. | |
| 2014/0046543 A1 | 2/2014 | Watanabe et al. | |
| 2014/0233703 A1* | 8/2014 | Omura ................. | A61B 6/4405 378/98 |
| 2014/0324315 A1 | 10/2014 | Brømdum | |
| 2016/0000390 A1* | 1/2016 | Uchida ................. | A61B 6/4405 378/119 |

FOREIGN PATENT DOCUMENTS

| | | |
|---|---|---|
| JP | H2-7068 U | 1/1990 |
| JP | 3-178642 A | 8/1991 |
| JP | 2003-104182 A | 4/2003 |
| JP | 2005-131157 A | 5/2005 |
| JP | 2005-306190 A | 11/2005 |
| JP | 2009-284935 A | 12/2009 |
| JP | 2010-214126 A | 9/2010 |
| JP | 2012-029889 A | 2/2012 |
| JP | 2013-503778 A | 2/2013 |
| JP | 2014-533217 A | 12/2014 |
| JP | 2015-97728 A | 5/2015 |
| WO | 2001/010300 A1 | 2/2001 |

OTHER PUBLICATIONS

"Portable X-ray Imaging Device IPF-21", Toshiba Medical Supply Co., Ltd., [online], [Search on Jul. 30, 1999], Internet URL: http://www.toshiba-iryouyouhin.co.jp/tmeds/xrays/ipf21.html, total 3 pages.
Communication dated Sep. 20, 2016, from Japanese Patent Office in counterpart application No. 2015-228537.
Communication drafted Jan. 27, 2017, from Japanese Patent Office in counterpart application No. 2015-228537 Y.
Written Opinion of the International Searching Authority dated Sep. 27, 2016, in counterpart International Application No. PCT/JP2016/002484 Y.
International Search Report for PCT/JP2016/002484 dated Sep. 27, 2016.
International Preliminary Report on Patentability dated Apr. 3, 2018, in counterpart International Application No. PCT/JP2016/002484.

* cited by examiner

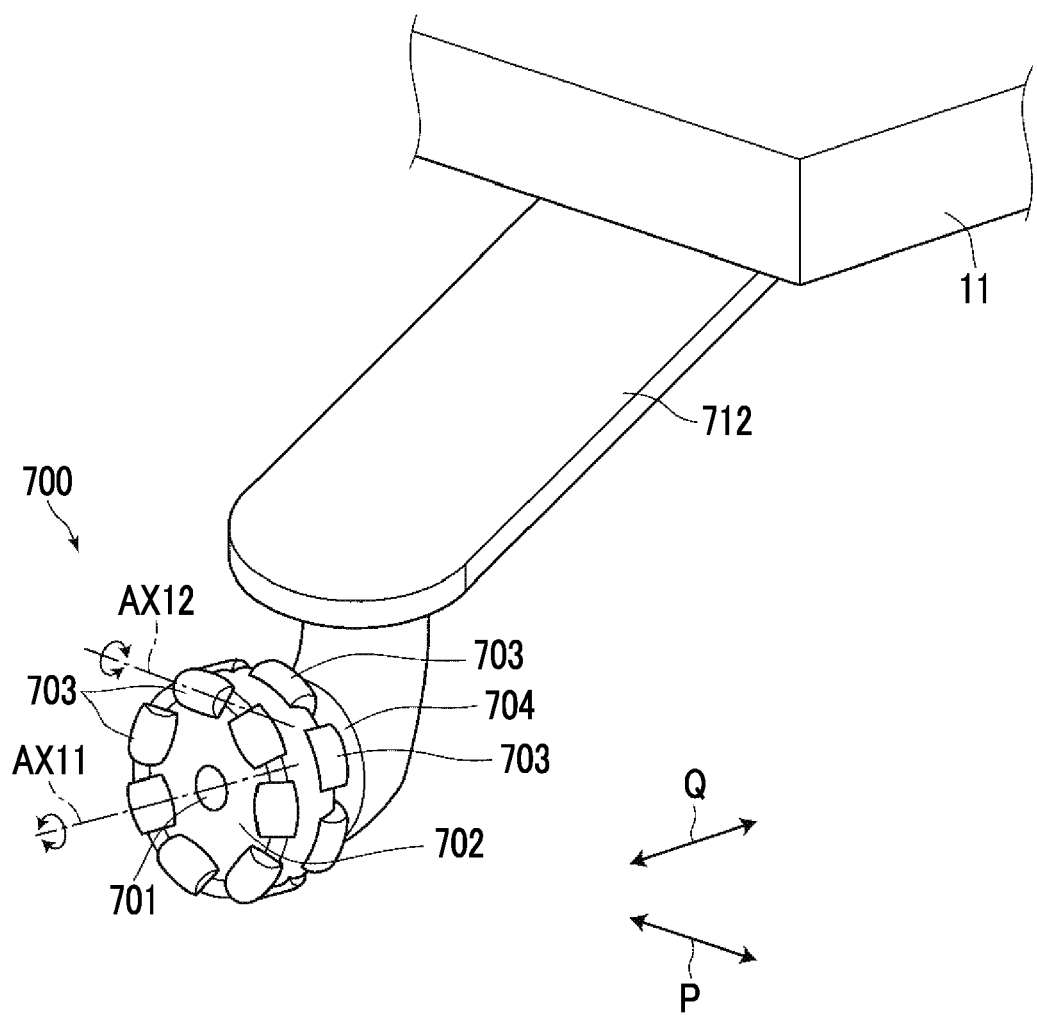

RADIATION-IRRADIATION DEVICE

CROSS-REFERENCE TO RELATED APPLICATIONS

This application is a continuation application of International Application No. PCT/JP2016/002484, filed on May 23, 2016, which is incorporated herein by reference in its entirety. Further, this application claims priority from Japanese Patent Application No. 2015-192067, filed on Sep. 29, 2015, and Japanese Patent Application No. 2015-228537, filed on Nov. 24, 2015, the disclosures of which are incorporated by reference herein.

BACKGROUND

Technical Field

The present invention relates to a radiation-irradiation device that irradiates a subject with radiation in a case in which the radiation image of the subject is to be acquired.

Related Art

In the past, a portable radiation-irradiation device, on which only a minimum number of components for radiation irradiation, such as a radiation source and an electrical circuit, are mounted and which can be operated while being held with hands by an operator, has been proposed as disclosed in, for example, JP2012-029889A and "Toshiba Medical Supply Co., Ltd., X-ray equipment IPF-21, [online], [Search on Jul. 30, 1999], Internet URL:http://www-.toshiba-iryouyouhin.co.jp/tmeds/xrays/ipf21.html". Since this kind of portable radiation-irradiation device is reduced in weight so that an operator can hold and operate the radiation-irradiation device with hands, the radiation-irradiation device is advantageous for the imaging of a subject in various directions.

A radiation detector (so-called "Flat Panel Detector"), which records a radiation image representing a subject by being irradiated with radiation transmitted through the subject, is generally used in a case in which the radiation image of the subject is to be taken by this kind of radiographic imaging apparatus. A cassette-type radiation detector having a structure in which an image detection unit and a control unit, such as a battery for drive and an electrical circuit relating to drive, are received in a housing is well known as the radiation detector. Further, in a case in which such a radiation detector is disposed at a position facing the radiation-irradiation device with a subject interposed therebetween and the radiation-irradiation device is driven in this state, the radiation detector is irradiated with radiation transmitted through the subject. Accordingly, a radiation image represented by the radiation transmitted through the subject is acquired.

The portable radiation-irradiation device can be held and operated with hands by an operator. However, a radiation-irradiation device, which includes a holding unit holding a radiation source unit including a radiation source, is proposed to prevent shaking and to prevent operator's hands or the like from being exposed to radiation. "Toshiba Medical Supply Co., Ltd., X-ray equipment IPF-21, [online], [Search on Jul. 30, 1999], Internet URL:http://www.toshiba-iryouyouhin.co.jp/tmeds/xrays/ipf21.html" also discloses an example of such a holding unit, and particularly, a holding unit that includes wheel parts provided at lower portions of holding legs and can travel.

The radiation-irradiation device including the holding unit basically includes: a leg unit that is adapted to be capable of traveling using wheels; a body unit that receives a control unit including a battery for the drive of a radiation source, an electrical circuit relating to the drive of the radiation source, and the like and is held on the leg unit; an arm unit serving as a holding unit that is connected to the body unit; and the like. The radiation source unit is mounted on the distal end of the holding unit, such as the arm unit.

In a case in which the radiation-irradiation device, which is adapted to be capable of traveling as described above, is used to take a radiation image, the radiation-irradiation device is transported to an imaging site by a transport force of an operator (user) or power. However, the collision or interference between the radiation-irradiation device and a transport path or obstacles, which are present near the transport path, should be naturally avoided during the transport of the radiation-irradiation device. Further, there is a case where the direction of the radiation-irradiation device is required to be finely adjusted so that the radiation-irradiation device is appropriately directed to a subject (object) or the like after the radiation-irradiation device reaches a place at which a radiation image is to be taken.

A method, which obliquely changes the direction of the radiation-irradiation device by rotationally moving the radiation-irradiation device about one of, for example, four wheels as an axis on a device-placement surface as a whole, is thought in order to respond to the above-mentioned request.

For example, JP2009-284935A discloses an X-ray imaging device for round visit in which X-ray imaging means for generating X-rays and irradiating an examinee with X-rays is mounted on a carriage adapted to be capable of traveling using wheels and which includes means for moving the X-ray imaging device so as to obliquely change the direction of the ray imaging device as a whole. Specifically, the means for moving the X-ray imaging device is formed of motors that drive a plurality of wheels in directions opposite to each other, and the like.

Further, JP2010-214126A discloses a movable X-ray imaging device in which an arm is mounted on a carriage adapted to be capable of traveling using casters including wheels and an X-ray generator is held on the arm and which irradiates a subject with X-rays generated from the X-ray generator and includes a brake pedal for locking the traveling rotation of the wheels of the casters. In this movable X-ray imaging device, an operator locks the traveling rotation of the wheels by stepping on the brake pedal in a case in which an X-ray image is to be taken. Accordingly, it is possible to prevent the position of the X-ray imaging device from changing.

However, since the X-ray imaging device disclosed in JP2009-284935A requires the motors for driving the plurality of wheels in directions opposite to each other, control units for these motors, and the like, high costs are required to move the X-ray imaging device so that the direction of the X-ray imaging device is obliquely changed.

On the other hand, since the movable X-ray imaging device disclosed in JP2010-214126A is adapted so that the traveling rotation of the plurality of casters mounted on the carriage is merely made to be capable of being performed or not capable of being performed, the X-ray imaging device is not particularly considered to move so that the direction of the X-ray imaging device is obliquely changed.

SUMMARY

The invention has been made in consideration of the circumstances, and an object of the invention is to provide a radiation-irradiation device of which a direction can be easily changed obliquely with a simple structure.

A radiation-irradiation device according to the invention comprises a base, an arm unit that is mounted on the base and is capable of elongating and contracting in a plan view, a radiation source that is mounted on the arm unit, and a wheel unit that is mounted on the base and allows the base to travel on a device-placement surface. The wheel unit includes a front wheel unit and at least two rear wheel units that are positioned on a rear side of the front wheel unit in a case in which an elongation direction of the arm unit in the plan view is forward and are away from each other in a direction crossing the elongation direction of the arm unit. Each of the rear wheel units includes a wheel that performs traveling rotation for the traveling, and a traveling direction-changing part that changes a direction of the traveling. Each of the rear wheel units further includes first locking means for restraining the traveling rotation of the wheel, and second locking means capable of operating independently of the first locking means and restraining an operation of the traveling direction-changing part.

"In a plan view" means that the arm unit is viewed on the device-placement surface in a case in which the arm unit is projected onto the device-placement surface.

Further, "elongating and contracting" means not only the linear elongation and contraction of the arm unit but also the fact that the arm unit takes a folded state and a state in which the arm unit is unfolded from the folded state and elongates.

Furthermore, "capable of elongating and contracting in a plan view" means that the arm unit is capable of elongating and contracting in a direction in which the arm unit elongates and contracts on a projection plane viewed in a plan view.

Further, the above-mentioned three "mounted" includes not only a case in which an element is directly mounted but also a case in which an element is indirectly mounted through something.

Furthermore, "elongation direction" means a direction in which the arm unit elongates at the center of the range of the rotational movement of the arm unit in a case in which the arm unit is rotationally movable in a plan view.

In the radiation-irradiation device of the invention, it is preferable that the rear wheel unit is formed of a revolving caster and the traveling direction-changing part is a revolving part of the revolving caster.

Alternatively, the rear wheel unit may be formed of OMNI WHEEL (registered trademark), and the traveling direction-changing part may be a roller that is mounted on a wheel body of the OMNI WHEEL.

Further, it is preferable that the radiation-irradiation device of the invention further includes an operating portion including operating pieces receiving an operating force applied from the outside and operating the first and second locking means, the operating portion is provided with a plurality of the operating pieces, and at least one of the plurality of operating pieces is disposed on each of front and rear sides of a middle position of the base in a forward direction and a rearward direction.

The above-mentioned "forward" means the elongation direction of the arm unit in a plan view as described above, and "rearward" means a direction opposite to the "forward".

Further, in a case in which the above-mentioned structure is applied, it is more preferable that the operating piece is disposed on a rear side of a rear end of the base and the operating piece is disposed on a front side of a front end of the base.

Furthermore, in a case in which the above-mentioned structure is applied, it is more preferable that the plurality of operating pieces interlock with each other.

Further, in the radiation-irradiation device of the invention, it is preferable that each of the rear wheel units is provided with a locking-operating part for one wheel exclusively taking a first state in which at least the first locking means is operated and a second state in which the second locking means is operated.

Alternatively, in the radiation-irradiation device of the invention, each of the rear wheel units may be provided with a locking-operating part for one wheel that exclusively takes a first state in which at least the first and second locking means are operated and a second state in which the second locking means is operated.

It is preferable that the above-mentioned locking-operating part for one wheel includes a seesaw-like operating piece oscillating about one fulcrum, takes the first state in a case in which the operating piece oscillates about the fulcrum in one direction, takes the second state in a case in which the operating piece oscillates about the fulcrum in the other direction, and takes a third state in which the first and second locking means are not operated in a case in which the operating piece does not oscillate not only in one direction but also in the other direction.

It is preferable that the radiation-irradiation device of the invention further includes a locking-operating part for a plurality of wheels operating the respective second locking means of the rear wheel units in parallel. "In parallel" means that a period in which operation times of the respective locking means overlap each other is present if only a little.

Further, it is preferable that two front wheel units are provided and two rear wheel units are provided in the radiation-irradiation device of the invention.

Alternatively, one front wheel unit may be provided and two rear wheel units may be provided.

Since the radiation-irradiation device of the invention includes first locking means for restraining the traveling rotation of the wheel of the rear wheel unit and second locking means capable of operating independently of the first locking means and restraining an operation of the traveling direction-changing part, the direction of the radiation-irradiation device can be easily changed.

Further, since the radiation-irradiation device of the invention does not require complicated mechanisms, such as motors for driving a plurality of wheels in directions opposite to each other and control units for these motors, the structure of the radiation-irradiation device can be made simple.

Since the centroid of the radiation-irradiation device is present close to the front side in a direction in which the arm unit elongates and contracts in a case in which the radiation-irradiation device is made to travel in a state in which the arm unit elongates, the device is likely to be shaken in a case in which the position of the radiation-irradiation device is to be adjusted. However, in a case in which the radiation-irradiation device is rotationally moved about one rear wheel unit as an axis as described above, the position of the radiation-irradiation device can be adjusted while the shake of the device is prevented and the radiation-irradiation device is stably kept.

BRIEF DESCRIPTION OF THE DRAWINGS

FIG. 20 is a perspective view of a rear wheel that is used in a radiation-irradiation device according to a seventh embodiment of the invention.

DESCRIPTION OF EMBODIMENTS

Embodiments of the invention will be described below with reference to the drawings.

First Embodiment

Figure 1:
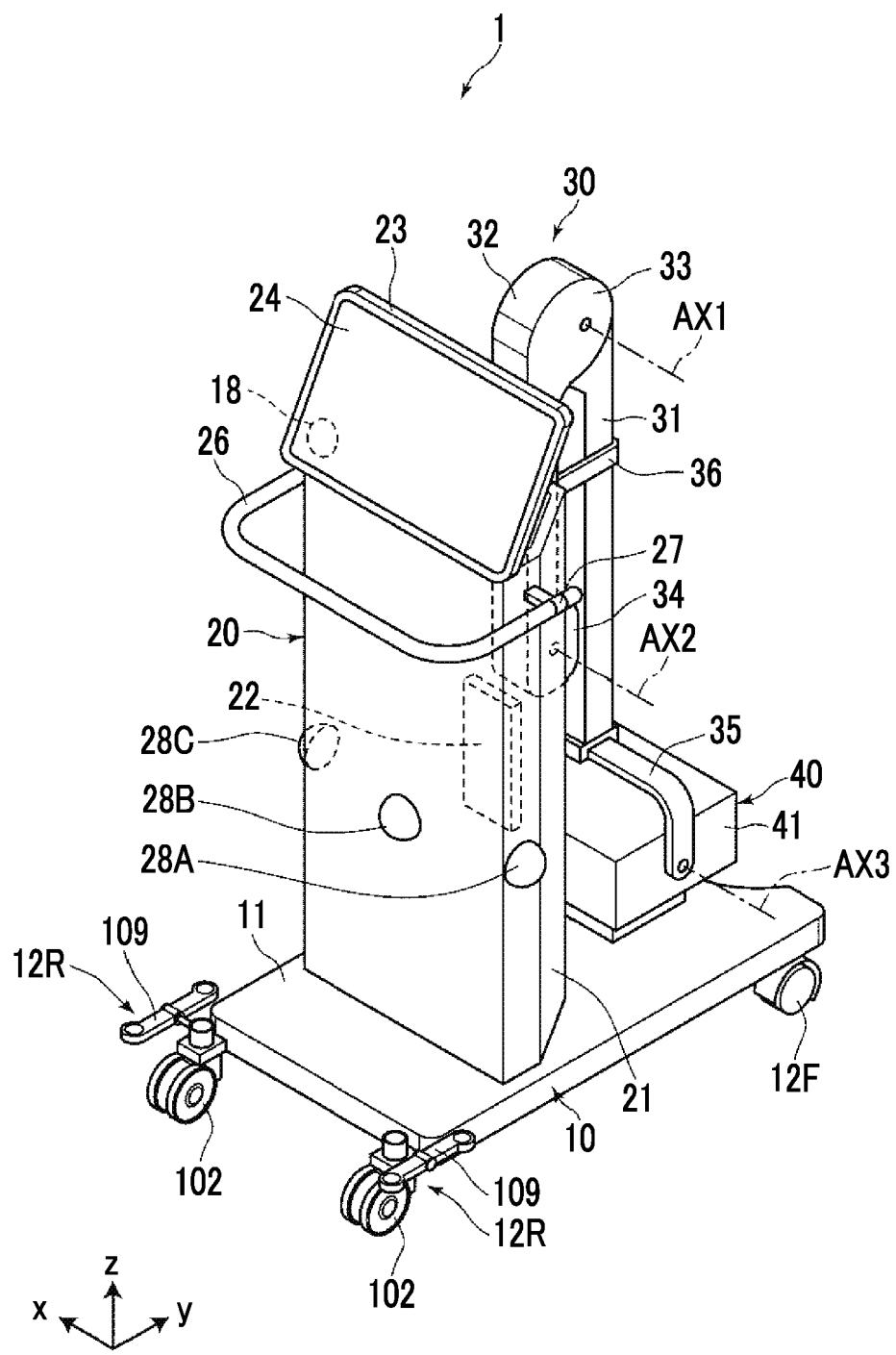
FIG. 1 is a perspective view showing the shape of the entire radiation-irradiation device according to a first embodiment of the invention.
Figure 2:
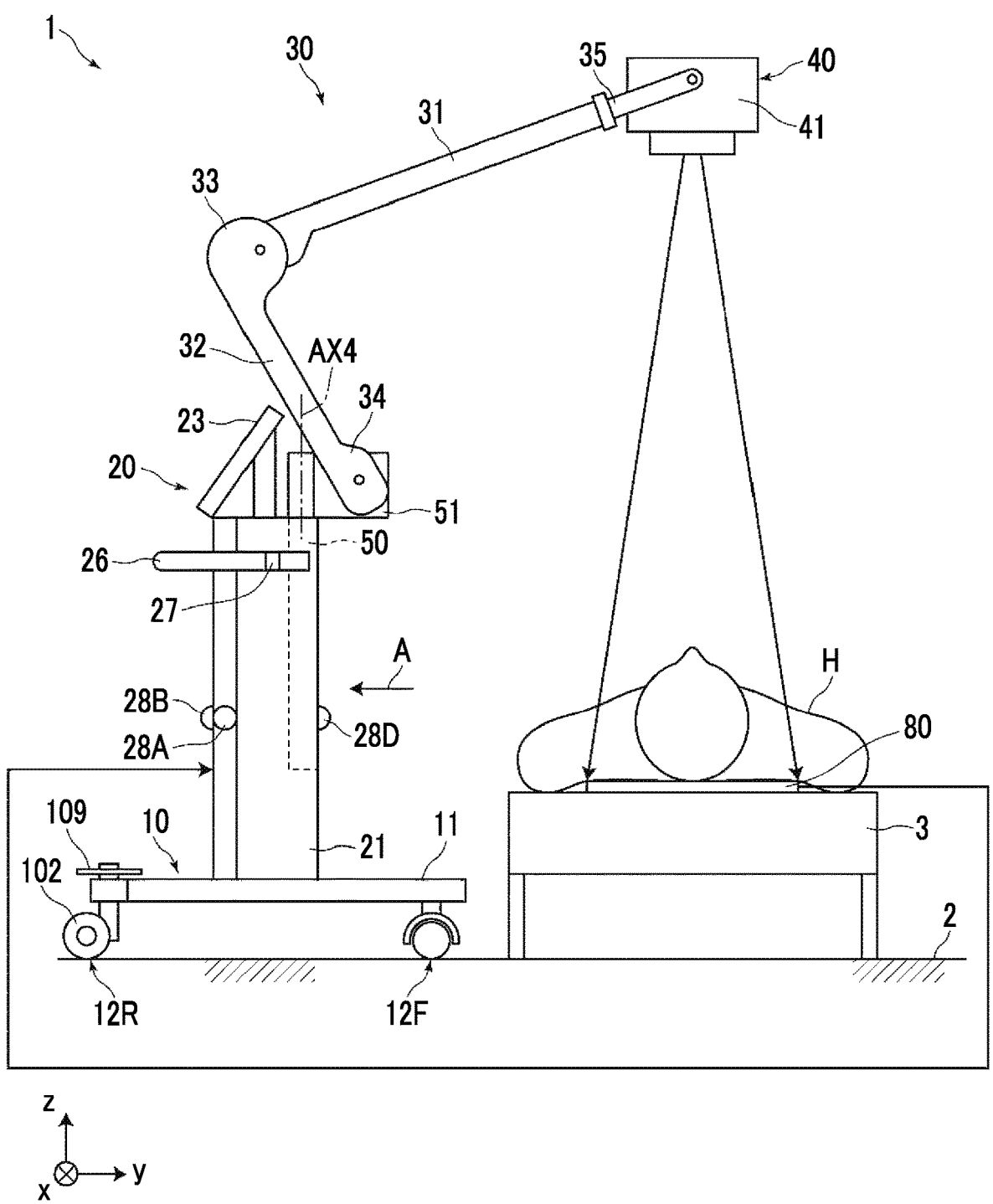
FIG. 2 is a side view showing a state in which the radiation-irradiation device is in use.

FIG. 1 is a perspective view showing the shape of the entire radiation-irradiation device 1 according to a first embodiment of the invention that is not in use, and FIG. 2 is a side view showing a state in which the radiation-irradiation device 1 is in use. In the following description, the upper side and the lower side in a vertical direction in a state in which the radiation-irradiation device 1 is placed on a device-placement surface 2, such as the floor of, for example, a medical facility, are referred to as "upper" and "lower", and a direction perpendicular to the vertical direction in the same state as the state is referred to as a "horizontal" direction. Further, the vertical direction is defined as a z direction, a lateral direction of FIG. 2 is defined as a y direction, and a direction perpendicular to the plane of FIG. 2 is defined as an x direction in the following description.

As shown in FIGS. 1 and 2, the radiation-irradiation device 1 of this embodiment includes a leg unit 10, a body unit 20, an arm unit 30 serving as a radiation source holding unit, and a radiation source unit (radiation source) 40.

The leg unit 10 can travel on the device-placement surface 2, and includes a plate-like base 11 and four wheel units that are mounted on portions of the base 11 close to four corners. These wheel units are two front wheel units 12F and two rear wheel units 12R. As in the case of a general revolving caster, each the front and rear wheel units 12F and 12R includes a wheel, such as a rubber tire, a revolving part that holds the wheel so as to allow the wheel to travel and rotate, and the like. The revolving part is mounted on the base 11 so as to be revolvable about an axis, which extends in the vertical direction, in a horizontal plane. Accordingly, the leg unit 10 is adapted to be capable of traveling on the device-placement surface 2 in an arbitrary direction. The structure of the front and rear wheel units 12F and 12R will be described in detail later.

The body unit 20 is installed on the leg unit 10, and includes a housing 21. A control unit 22, which controls the drive of the radiation-irradiation device 1, and a battery (not shown) are received in the housing 21. The control unit 22 is a unit that is used to control not only the dose, the irradiation time, and the like of radiation generated from the radiation source unit 40 but also various operations of the radiation-irradiation device 1. The control unit 22 is formed of, for example, a computer in which a program for control is installed, dedicated hardware, or a combination of both the computer and the dedicated hardware. Further, a monitor 23 in which a speaker 18 is built is mounted on the upper surface of the housing 21. A handle 26, which is used to push or pull the radiation-irradiation device 1, is mounted on the upper portion of the housing 21 through an adapter 27. Furthermore, cameras 28A, 28B, 28C, and 28D, which are used to take an omnidirectional image of the device 1, are mounted on the right side surface, the rear surface, the left side surface, and the front surface of the body unit 20, respectively. For example, a digital video camera, which outputs digital signals representing a taken video, is used as each of these cameras 28A to 28D. However, the camera is not limited thereto, and a digital still camera may be applied.

The monitor 23 serving as display means is formed of a liquid crystal panel or the like, and displays a radiation image that is acquired from the imaging of a subject H and various kinds of information that is required for the control of the device 1. Further, the monitor 23 includes a touch panel type input unit 24, and receives the input of various commands required for the operation of the device 1. The monitor 23 is mounted on the upper surface of the body unit 20 so that the inclination and the rotational position of the monitor 23 are changeable. Videos or still images, which are taken by the cameras 28A to 28D, are displayed on the monitor 23. Furthermore, an operator can grasp a situation around the radiation-irradiation device 1 with reference to the images displayed on the monitor 23.

The arm unit 30 is held on the body unit 20. In detail, the arm unit 30 is held on the surface of the body unit 20 opposite to the handle 26, that is, a right surface of the body unit 20 in FIG. 2. The arm unit 30 is adapted to be capable of being raised and lowered relative to the body unit 20 by a raising/lowering mechanism 50 that is formed of, for example, a pantograph mechanism or the like. The arm unit 30 includes a first arm 31, a second arm 32, a first rotational moving portion 33, a second rotational moving portion 34, and a radiation source holding part 35. The radiation source unit 40 is held at the distal end of the first arm 31 through the radiation source holding part 35. In the following description, an end portion of the first arm 31 close to the radiation source unit 40 is referred to as an upper end portion and an end portion of the first arm 31 close to the second arm 32 is referred to as a lower end portion. Further, an end portion of the second arm 32 close to the first arm 31 is referred to as an upper end portion and an end portion of the second arm 32 close to the body unit 20 is referred to as a lower end portion.

The first and second arms 31 and 32 are connected to each other by the joint-like first rotational moving portion 33 so as to be rotationally movable about a rotational movement axis AX1. The rotational movement axis AX1 is an axis extending in the x direction. The first arm 31 is rotationally moved about the rotational movement axis AX1 so that an angle between the first and second arms 31 and 32 is changed. The first rotational moving portion 33 holds both the first and second arms 31 and 32 so that the first arm 31 is rotationally moved relative to the second arm 32 through a friction mechanism. For this reason, the first arm 31 is rotationally movable in a case in which an external force, which is strong to some extent, is applied to the first arm 31, and maintains an angle relative to the second arm 32 without being rotationally moved as long as an external force is not applied to the first arm 31.

The second arm 32 is connected to an adapter 51, which is mounted on the upper end portion of the raising/lowering mechanism 50, through the joint-like second rotational moving portion 34 so as to be rotationally movable about a rotational movement axis AX2. The rotational movement axis AX2 is an axis extending in the x direction. The second arm 32 is rotationally moved in a yz plane about the rotational movement axis AX2 so that an angle between the second arm 32 and the surface of the body unit 20 on which the arm unit 30 is held is changed. The second rotational moving portion 34 holds both the second arm 32 and the adapter 51 so that the second arm 32 is rotationally moved relative to the adapter 51 through a friction mechanism. For this reason, the second rotational moving portion 34 is rotationally movable in a case in which an external force, which is strong to some extent, is applied to the second rotational moving portion 34, and maintains an angle relative to the body unit 20 without being rotationally moved as long as an external force is not applied to the second rotational moving portion 34.

Figure 3:
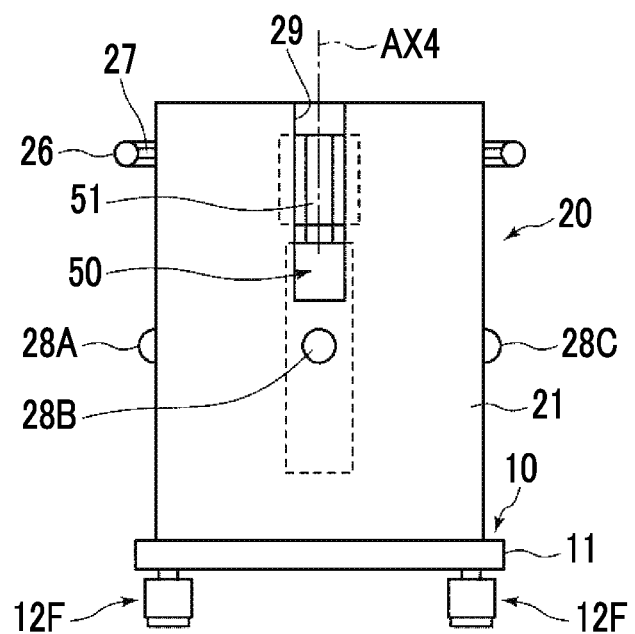
FIG. 3 is a diagram viewed in the direction of an arrow A of FIG. 2.

FIG. 3 shows a state in which a part of the radiation-irradiation device 1 is viewed in the direction of an arrow A of FIG. 2. As shown in FIG. 3, a groove 29, through which the adapter 51 can pass at the time of an operation for raising and lowering the arm unit 30 performed by the raising/lowering mechanism 50, is formed on the right surface of the body unit 20 in FIG. 2. For illustration, the monitor 23 and the arm unit 30 are not shown in FIG. 3.

Returning to FIGS. 1 and 2, description will be continued. The radiation source holding part 35 is formed in a substantially U shape, and is mounted on the distal end of the first arm 31. The radiation source unit 40 is connected to the distal end of the first arm 31 through the radiation source holding part 35 so as to be rotationally movable about a rotational movement axis AX3. The rotational movement axis AX3 is an axis extending in the x direction. The radiation source unit 40 is rotationally moved about the rotational movement axis AX3 so that an angle between the radiation source unit 40 and the first arm 31 is changed. The radiation source holding part 35 holds both the radiation source unit 40 and the first arm 31 so that the radiation source unit 40 is rotationally moved relative to the first arm 31 through a friction mechanism. For this reason, the radiation source unit 40 is rotationally movable in a case in which an external force, which is strong to some extent, is applied to the radiation source unit 40, and maintains an angle relative to the first arm 31 without being rotationally moved as long as an external force is not applied to the radiation source unit 40.

Furthermore, the adapter 51 is connected to the raising/lowering mechanism 50 so as to be rotationally movable about a rotational movement axis AX4. The rotational movement axis AX4 is an axis extending in the z direction. The adapter 51 is rotationally moved in an xy plane about the rotational movement axis AX4. In a case in which the adapter 51 is rotationally moved in this way, the entire arm unit 30 is rotationally moved in the xy plane. The adapter 51 holds both the second arm 32 and the raising/lowering mechanism 50 so that the second arm 32 is rotationally moved relative to the raising/lowering mechanism 50 through a friction mechanism. For this reason, the arm unit 30 connected to the adapter 51 is rotationally movable in a case in which an external force, which is strong to some extent, is applied to the arm unit 30, and maintains a rotational movement position thereof in the xy plane without being rotationally moved as long as an external force is not applied to the arm unit 30.

As described above, in this embodiment, each of the rotational movement of the first arm 31 relative to the second arm 32, the rotational movement of the second arm 32 relative to the body unit 20 in the yz plane, the rotational movement of the radiation source unit 40 relative to the first arm 31, and the rotational movement of the entire arm unit 30 relative to the raising/lowering mechanism 50 in the xy plane is achieved through the friction mechanism. However, rotational movement positions may be fixed by publicly known lock mechanisms. In this case, it is possible to rotationally move the first arm 31, the second arm 32, the radiation source unit 40, and the entire arm unit 30 by releasing the lock mechanisms. Further, it is possible to fix the rotational movement positions by locking the lock mechanisms at desired rotational movement positions.

FIG. 1 shows a state in which the radiation-irradiation device 1 is not in use, and the arm unit 30 is positioned at an initial position in a case in which the radiation-irradiation device 1 is not in use. The initial position of the arm unit 30 is a position where the entire arm unit 30 is present so as to be away from the raising/lowering mechanism 50 in the y direction and is positioned at the lowest position among the positions where the arm unit 30 is positioned in the vertical direction by the raising/lowering mechanism 50 in a state in which the first and second arms 31 and 32 are folded. Particularly, in this embodiment, the initial position is set to the position of the arm unit 30 in a state in which the first and second arms 31 and 32 are folded to a limit where the first and second arms 31 and 32 are not rotationally moved any more as shown in FIG. 1. At the initial position, the second arm 32 is in a state in which the first rotational moving portion 33 is positioned above the second rotational moving portion 34.

Here, a position where the entire arm unit 30 is present so as to be away from the raising/lowering mechanism 50 in the +y direction is referred to as the initial rotational movement position of the arm unit 30. The +y direction is a right direction in FIG. 2. The arm unit 30 is rotationally movable about the rotational movement axis AX4 from the initial rotational movement position in the xy plane as described above. The rotational movement is performed about the rotational movement axis AX4 in the range of 45° in a clockwise direction to 45° in a counterclockwise direction.

The first and second arms 31 and 32 are fastened to each other by a fastening belt 36 at the initial position. For example, one end portion of the fastening belt 36 is mounted on the second arm 32 and a hook-and-loop fastener is mounted on the other end portion of the fastening belt 36. A hook-and-loop fastener corresponding to the hook-and-loop fastener of the fastening belt 36 is mounted on the surface of the first arm 31 opposite to the surface of the first arm 31 shown in FIG. 1. Further, the fastening belt 36 is put around the first arm 31 from the right surface of the first arm 31 in FIG. 1 to the opposite surface of the first arm 31 to connect the hook-and-loop fastener of the fastening belt 36 to the hook-and-loop fastener mounted on the first arm 31. Accordingly, the first arm 31 is not rotationally moved relative to the second arm 32 at the initial position.

Figure 4:
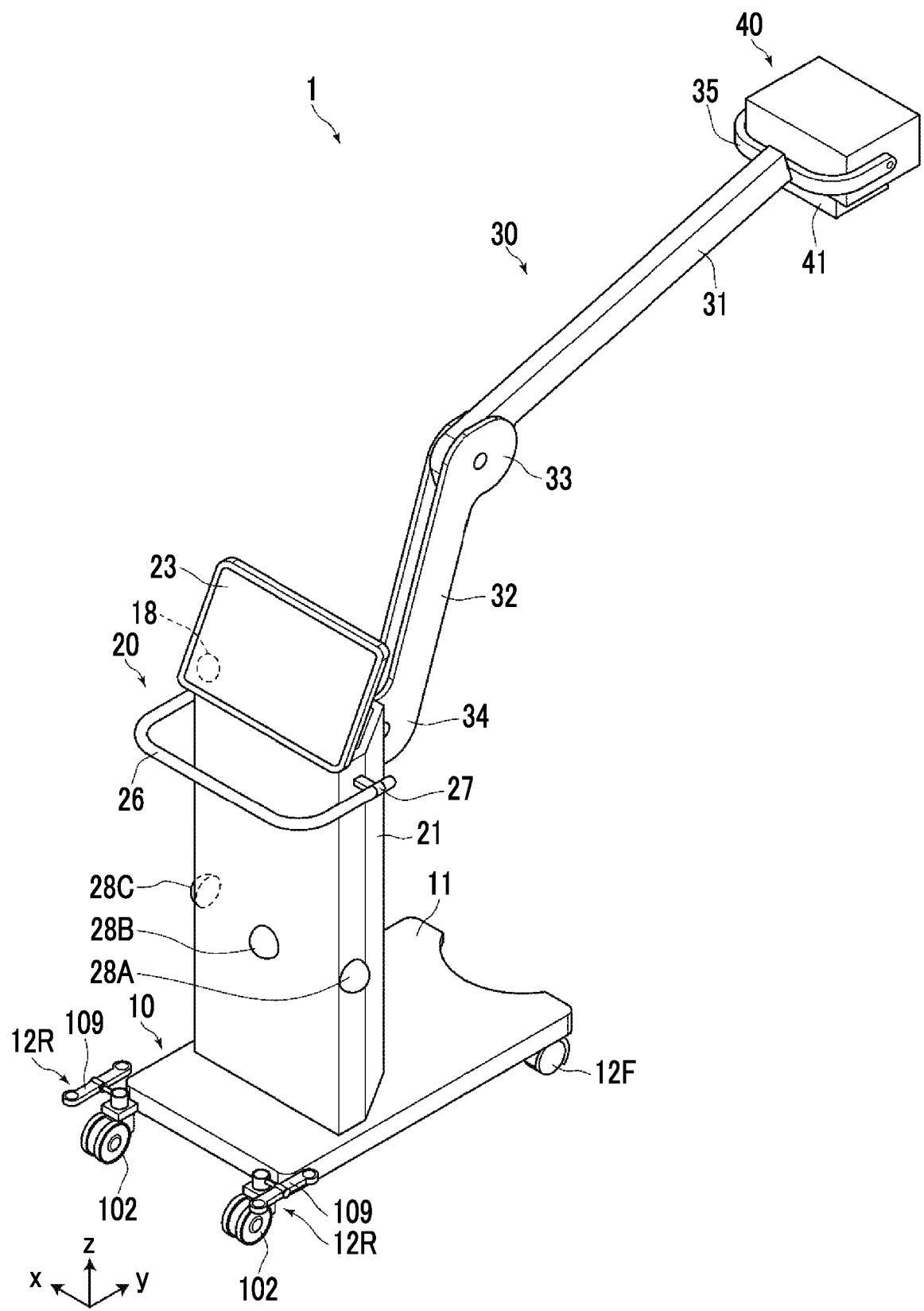
FIG. 4 is a perspective view showing an example of a state in which the radiation-irradiation device is in use.

In a case in which the radiation-irradiation device 1 is used, the arm unit 30 is shifted from the initial position to a use position at which the first and second arms 31 and 32 are unfolded. FIG. 4 shows the radiation-irradiation device 1 of which the arm unit 30 is set to one example of the use position.

The radiation source unit 40 has a structure where a radiation source, a collimator for narrowing the irradiation range of radiation, and the like are received in a housing 41. The radiation source includes, for example, an X-ray tube, a booster circuit, cooling means for cooling the X-ray tube, and the like. The emission of radiation from the radiation source of the radiation source unit 40 is performed by a command that is input from the input unit 24 of the monitor 23 by an operator. The input unit 24 is used to input information that is required to perform various operations of the radiation-irradiation device 1, and forms a console (operator console), which is used to perform the management of imaging orders, the image processing of a taken image, the display of the taken image, and the like, together with the control unit 22 and the monitor 23.

In this embodiment, in a case in which the radiation image of a subject H is to be taken, a radiation detector 80 is disposed under a subject H supine on a bed 3 as shown in FIG. 2 and is irradiated with radiation, such as, X-rays, emitted from the radiation source of the radiation source unit 40 and passing through the subject H.

Figure 5:
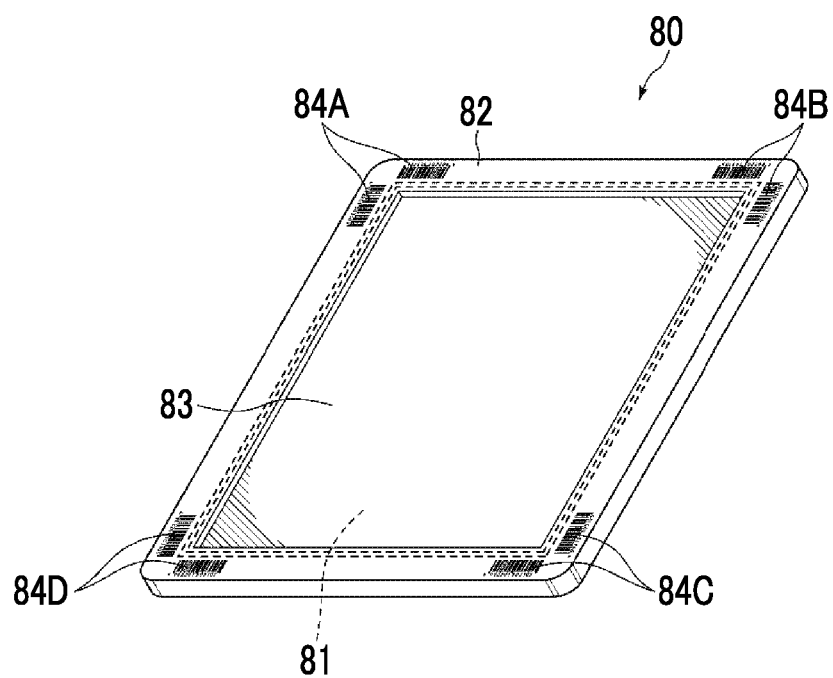
FIG. 5 is a perspective view showing the appearance of a radiation detector viewed from a front surface that is a radiation-irradiation side.

The radiation detector 80 will be briefly described here with reference to FIG. 5. FIG. 5 is a perspective view showing the appearance of the radiation detector viewed from a front surface that is a radiation-irradiation side. As shown in FIG. 5, the radiation detector 80 of this embodiment is a cassette-type radiation detector that includes an image detection unit 81 serving as a radiation image recording medium and a housing 82 receiving the image detection unit 81. As well known, the image detection unit 81 includes a scintillator (phosphor) that converts incident radiation into visible light and a thin-film-transistor (TFT) active matrix substrate. A rectangular imaging region in which a plurality of pixels for accumulating electric charges corresponding to visible light emitted from the scintillator are arranged is formed on the TFT active matrix substrate. In the radiation detector 80, the image detection unit 81 is a radiation image recording medium. However, for convenience' sake, the entire radiation detector 80 may also be called as a radiation image recording medium in this specification.

An imaging control unit, which includes a gate driver, a signal processing circuit, and the like, and the like are built in the housing 82 in addition to the image detection unit 81. The gate driver applies gate pulses to a gate of a TFT to switch the TFT. The signal processing circuit converts electric charges, which are accumulated in the pixels, into analog electrical signals, which represent an X-ray image, and outputs the analog electrical signals. Further, the housing 82 has substantially the same size as, for example, a film cassette, an imaging plate (IP) cassette, or a computed radiography (CR) cassette that is based on International Organization for Standardization (ISO) 4090:2001.

Markers 84A to 84D, which represent identification information for identifying the radiation detector 80, are given to four corners of a front surface 82A of the housing 82. In this embodiment, each of the markers 84A to 84D is formed of two bar codes orthogonal to each other. Further, the markers 84A to 84D may be adapted to transmit identification information by radio.

Next, an operation in a case in which a radiation image is not yet taken by the radiation-irradiation device 1 will be described. In the state which is shown in FIG. 1 and in which the radiation-irradiation device 1 is not in use, that is, in a state in which the arm unit 30 is stored, the radiation-irradiation device 1 is transported to a use position while being made to travel on the device-placement surface 2 by the front and rear wheel units 12F and 12R that travel and rotate. The transport of the radiation-irradiation device 1 is performed in a case in which an operator (device user) pushes or pulls the radiation-irradiation device 1 while holding the handle 26.

Here, "a state in which the arm unit 30 is stored" is a state in which the arm unit 30 is positioned at the above-mentioned initial position. In a case corresponding to emergency care or the like, the radiation-irradiation device 1 may be carried to the use position in the same manner as described above in a state in which the arm unit 30 is unfolded. Since each of the front and rear wheel units 12F and 12R is revolvably mounted on the base 11 as described above, the radiation-irradiation device 1 can be moved in a front-back direction and the lateral direction and can also be moved along a large curve. In addition, the radiation-irradiation device 1 can also revolve about a vertical axis passing through the base 11. Accordingly, the radiation-irradiation device 1 can be quickly transported to a use position in a state in which the radiation-irradiation device 1 travels in a small radius.

The taking of a radiation image is performed on the subject H who is supine on, for example, the bed 3 as shown in the above-mentioned FIG. 2. In a case in which the radiation-irradiation device 1 is to be set close to the subject H, the radiation-irradiation device 1 can also be moved in the height direction of the subject H by the front and rear wheel units 12F and 12R. Accordingly, the radiation-irradiation device 1 can be easily set at the optimum position.

Figure 6:
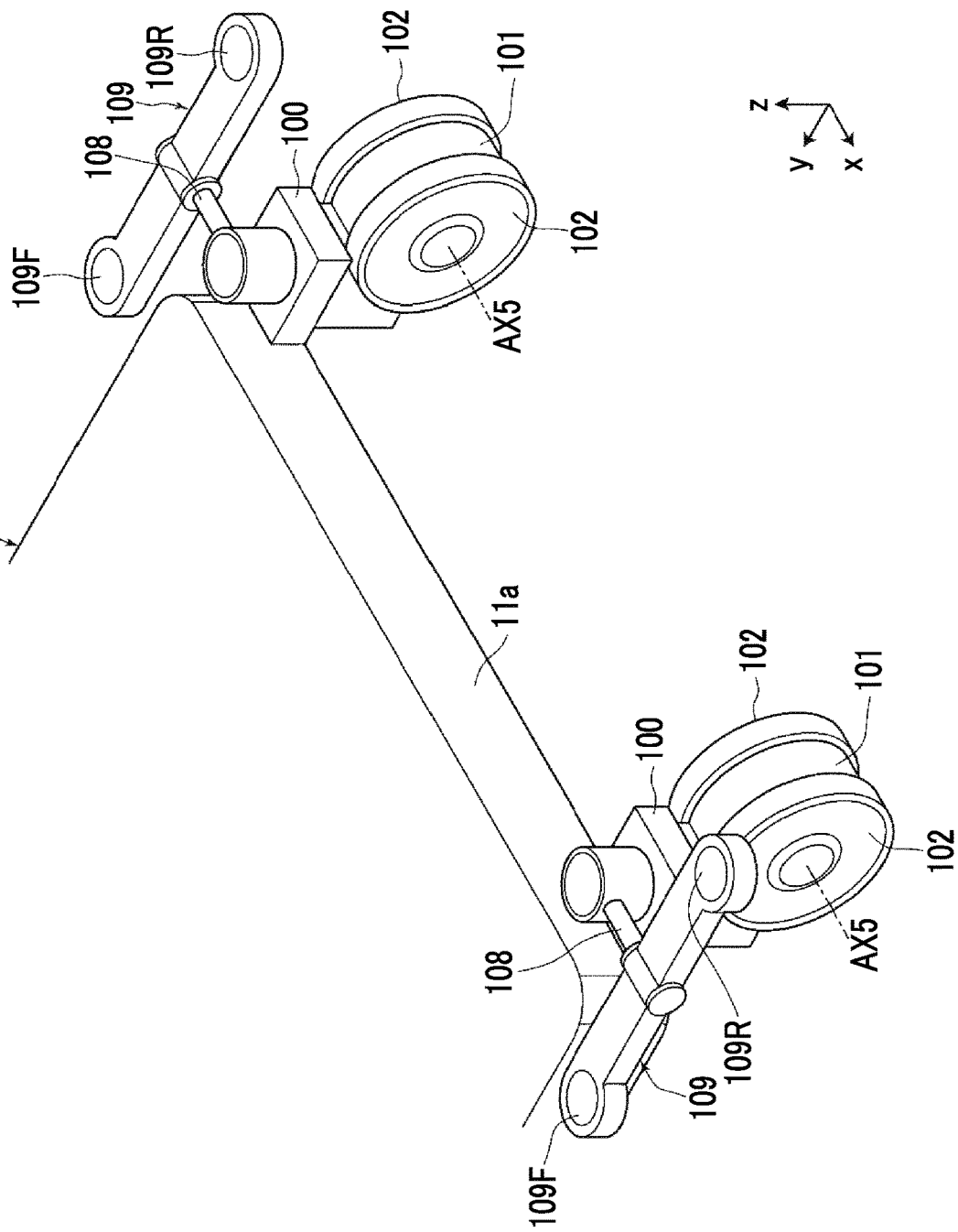
FIG. 6 is a perspective view showing peripheral portions of rear wheels of the radiation-irradiation device.
Figure 7:
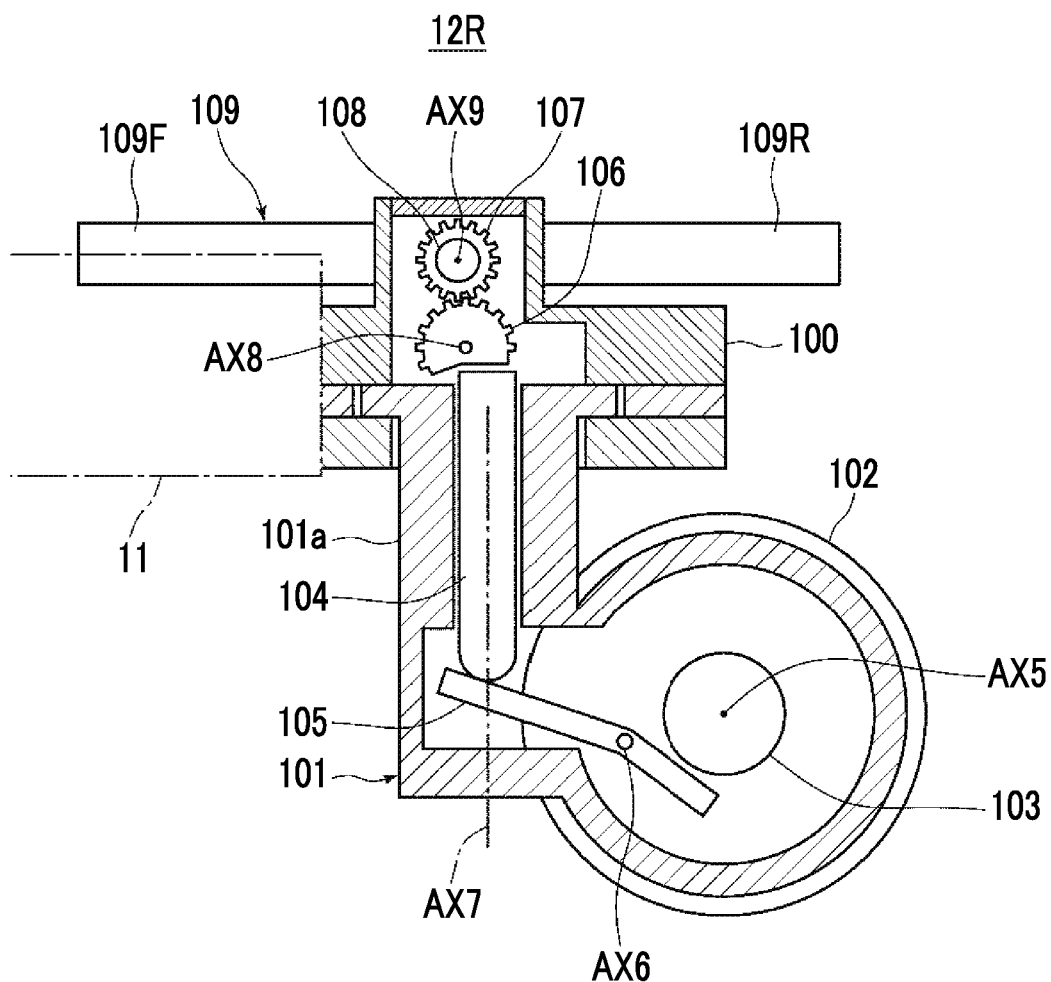
FIG. 7 is a partial cross-sectional side view of the rear wheel shown in FIG. 6.

Next, the structure of the rear wheel unit 12R of the radiation-irradiation device 1 of this embodiment will be described in detail with reference to FIGS. 6 to 9. FIG. 6 is a perspective view showing the appearance of the two rear wheel units 12R and peripheral portions thereof, and FIG. 7 is a partial cross-sectional side view showing the internal structure of one rear wheel unit 12R. As shown in FIGS. 6 and 7, the rear wheel unit 12R includes a holding portion 100 that is fixed to the rear end portion of the base 11, for example, a rear end face 11a, a casing 101 that is held by the holding portion 100 and serves as a traveling direction-changing part, and two wheels 102 that are held by the casing 101 so as to be capable of traveling and rotating about an rotation axis AX5.

A disc 103, a rod 104, and a lever 105 are received in the casing 101. The disc 103 is connected to the two wheels 102 and is rotated together with these wheels 102. The rod 104 is disposed in a cylindrical portion 101a of the casing 101 in a state in which the rod 104 extends in the vertical direction. The lever 105 is disposed in a state in which one end portion of the lever 105 is positioned under the rod 104 and the other end portion thereof is positioned close to the disc 103, and oscillates about an oscillation axis AX6. The cylindrical portion 101a of the casing 101 is held by the holding portion 100 so as to be revolvable about a revolution axis AX7 extending in an axial direction of the cylindrical portion at a position that does not cross the above-mentioned rotation axis AX5. The rod 104 is disposed in a state in which the major axis of the rod 104 coincides with the revolution axis AX7. The lever 105 is biased by biasing means (not shown) so as to oscillate about the oscillation axis AX6 in a clockwise direction in FIG. 7. Further, the rod 104 is biased upward in FIG. 7 by biasing means (not shown). As long as an external force is not applied to the rod 104 and the lever 105, the other end portion of the lever 105 is maintained in a state in which the other end portion of the lever 105 is slightly away from the disc 103.

A cam 106 and a gear 107 are received in the holding portion 100. The cam 106 includes a gear-shaped portion formed on a part of the outer peripheral surface thereof, is positioned above the rod 104, and is adapted to be rotationally movable about a rotational movement axis AX8. The gear 107 is disposed in a state in which the gear 107 meshes with the gear-shaped portion of the cam 106. The gear 107 is connected to a shaft 108 that is rotated about a rotation axis AX9. One end portion of the shaft 108 extends to the outside of the holding portion 100, and a brake pedal (operating piece) 109 is connected to one end portion of the shaft 108.

The brake pedal 109 oscillates in the form of a seesaw about the rotation axis AX9 as a fulcrum. That is, in a case in which a front operating portion 109F of the brake pedal 109 is pushed down by an operator's foot or the like, the brake pedal 109 oscillates about the rotation axis AX9 as a fulcrum so that the left end of the brake pedal 109 is lowered in FIG. 7. In a case in which a rear operating portion 109R of the brake pedal 109 is pushed down, the brake pedal 109 oscillates about the rotation axis AX9 as a fulcrum so that the right end of the brake pedal 109 is lowered in FIG. 7.

The brake pedal 109 may be adapted to maintain the oscillating state as described above only in a case in which the front operating portion 109F or the rear operating portion 109R is pushed. Alternatively, the brake pedal 109 may be adapted to maintain the oscillating state as described above in a case in which the front operating portion 109F (or the rear operating portion 109R) is pushed once, and to then release the oscillating state and return to a horizontal state in a case in which the other operating portion, that is, the rear operating portion 109R (or the front operating portion 109F) is pushed. However, considering workability, it is more preferable that the brake pedal 109 is adapted as in the latter.

Figure 8:
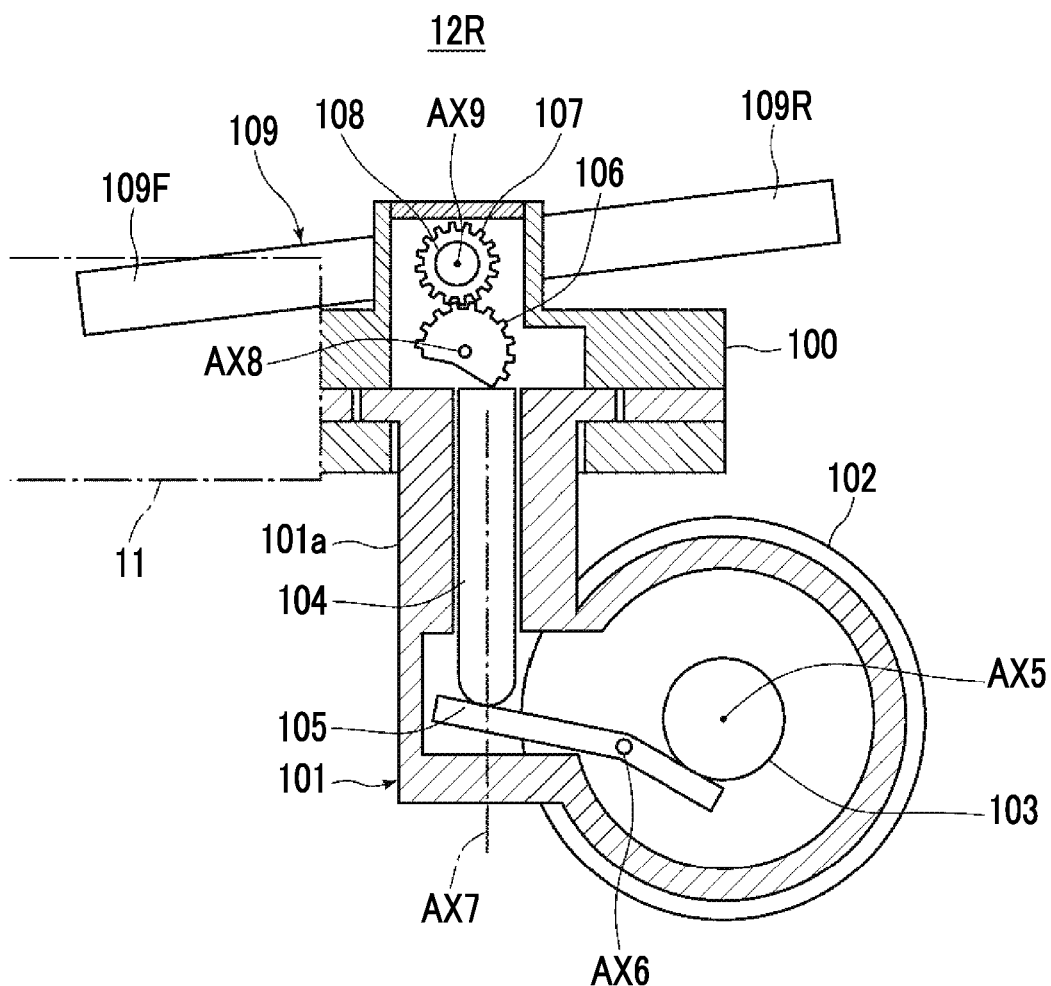
FIG. 8 is a partial cross-sectional side view showing that the rear wheel shown in FIG. 7 is in another state.

In a case in which the front operating portion 109F of the brake pedal 109 is operated to be pushed down in the rear wheel unit 12R having the above-mentioned structure, an operating force is transmitted to the cam 106 through the shaft 108 and the cam 106 is rotationally moved about the rotational movement axis AX8 in the clockwise direction in FIG. 7. A state in this case is shown in FIG. 8. The same components as the components described above in FIG. 7 and the like are denoted in FIG. 8 by the same reference numerals as the reference numerals of FIG. 7, and the description thereof will be omitted as long as being not particularly needed (the same hereinafter).

As shown in FIG. 8, the cam 106, which has been rotationally moved, pushes the rod 104 down against the above-mentioned biasing force. Accordingly, one end portion of the lever 105 is pushed by the rod 104, so that the lever 105 oscillates about the oscillation axis AX6 in a counterclockwise direction in FIG. 8. Therefore, the other end portion of the lever 105 presses the disc 103, so that the rotation of the disc 103, that is, the traveling rotation of the wheel 102 about the rotation axis AX5 (hereinafter, referred to as "the traveling rotation of the rear wheel unit 12R") is restrained. The state of the brake pedal 109 in this case is one example of a first state of the invention.

Figure 9:
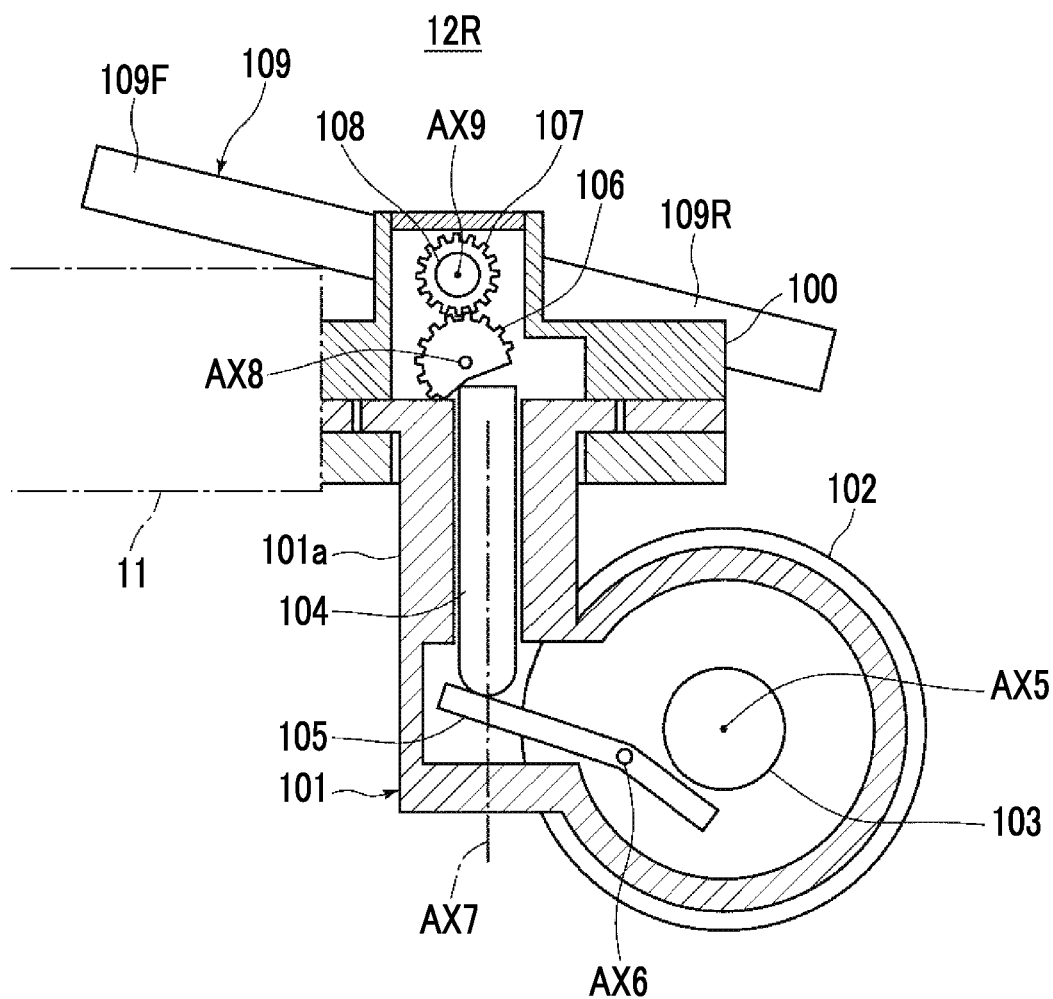
FIG. 9 is a partial cross-sectional side view showing that the rear wheel shown in FIG. 7 is in still another state.

On the other hand, in a case in which the rear operating portion 109R of the brake pedal 109 is operated to be pushed down, an operating force is transmitted to the cam 106 through the shaft 108 and the cam 106 is rotationally moved about the rotational movement axis AX8 in the counterclockwise direction in FIG. 7. A state in this case is shown in FIG. 9. As shown in FIG. 9, the cam 106, which has been rotationally moved, presses the upper end face of the cylindrical portion 101a of the casing 101. Accordingly, the revolution of the casing 101 is restrained, so that the revolution of the wheels 102 about the revolution axis AX7 (hereinafter, referred to as "the revolution of the rear wheel unit 12R") is restrained. The state of the brake pedal 109 in this case is one example of a second state of the invention.

Figure 10A:
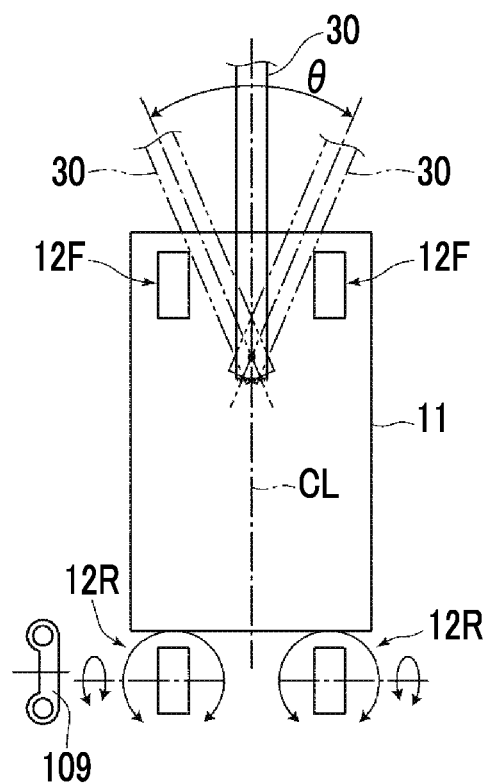
FIGS. 10A, 10B, and 10C are diagrams illustrating the operating states of the rear wheels of the radiation-irradiation device.
Figure 10B:
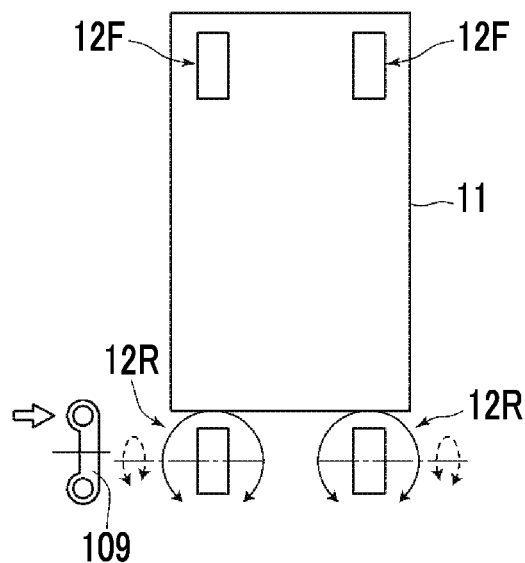
Figure 10C:
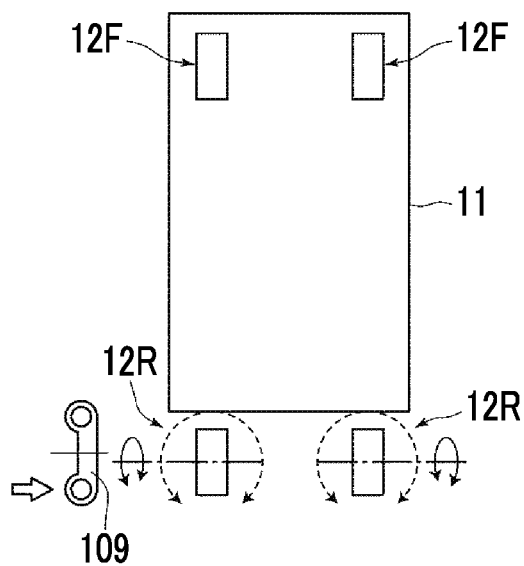

The first and second states having been described above will be described in detail with reference to FIGS. 10A, 10B, and 10C. FIGS. 10A, 10B, and 10C show whether or not the traveling rotation and revolution of the rear wheel units 12R can be performed. In FIGS. 10A, 10B, and 10C, the traveling rotation of the rear wheel unit 12R is shown by a small elliptical arrow and the revolution of the rear wheel unit 12R is shown by a large circular arrow. Among these arrows, an arrow shown by a solid line shows that each operation can be performed and an arrow shown by a broken line shows that each operation is restrained. Further, the operation state of the brake pedal 109 is shown in FIGS. 10A, 10B, and 10C together, the fact that an outline arrow is shown near the upper end of the brake pedal 109 in FIGS. 10A, 10B, and 10C means that the front operating portion 109F of the brake pedal 109 is operated to be pushed, and the fact that an outline arrow is shown near the lower end of the brake pedal 109 in FIGS. 10A, 10B, and 10C means that the rear operating portion 109R of the brake pedal 109 is operated to be pushed. Here, the operation state of only one brake pedal 109 is shown as a state in which the brake pedals 109 of the two rear wheel units 12R are operated in the same manner. Since the front wheel units 12F can not only travel and rotate but also revolve in this embodiment, the traveling rotation and revolution of the front wheel units 12F are not particularly shown and the description thereof will also be omitted. However, the radiation-irradiation device 1 of the invention is not limited thereto, and may be appropriately provided with locking means for suppressing at least one of the traveling rotation and revolution of the front wheel units 12F.

As shown in FIG. 10A, the arm unit 30 is rotationally movable in the range of an angle θ from a center line CL, which is parallel to the left and right long sides of the substantially rectangular base 11 and passes through the middle of the base 11 in the lateral direction (±x direction in FIG. 1), as the middle of a rotational movement range in a plan view (in a case in which the arm unit 30 is viewed so as to be projected onto the device-placement surface 2). This rotational movement is performed in a case in which the adapter 51 of FIG. 2 is rotationally moved relative to the raising/lowering mechanism 50 about the rotational movement axis AX4 as described above. Further, since the arm unit 30 can elongate and contract, that is, can be changed between the above-mentioned initial position (a state in which the arm unit 30 is folded and stored) and an unfolded position shown in FIG. 4 in the plan view, the arm unit 30 is adapted to be capable of elongating and contracting in a direction in which the arm unit 30 elongates and contracts on a projection plane in a case in which the change of the arm unit 30 is projected into the device-placement surface 2.

Since the two rear wheel units 12R are positioned on the rear side of the two front wheel units 12F in an elongation direction (+y direction in FIG. 1) in the plan view in a case in which the arm unit 30 is positioned in the middle of the rotational movement range, the two rear wheel units 12R are referred to as "rear wheels". In a case in which the arm unit 30 merely elongates and contracts without being rotationally moved, the wheel units, which are positioned on the front side in the elongation direction in the plan view of the arm unit 30 in regard to the elongation and contraction, are referred to as front wheels and the wheel units positioned on the rear side are referred to as rear wheels. The two rear wheel units 12R are disposed so as to be away from each other in a direction crossing a direction in which the arm unit 30 elongates as described above.

Further, the "elongation and contraction" of an arm unit of the invention does not means only the change of the arm unit between a folded state and an unfolded state as in the case of the arm unit 30 of this embodiment. For example, a linear change, which is caused by the forward and backward movement of an arm-distal end part, in the total length of an arm unit of which the rod-like arm-distal end part is received in a cylindrical arm-proximal end part and is moved forward and backward in the arm-proximal end part in the axial direction of the cylindrical arm-proximal end part also means the "elongation and contraction". Furthermore, a change in the total length of the arm unit, which is caused by a linear change in the total length of the arm unit in addition to the change of the arm unit between the folded state and the unfolded state, also means the "elongation and contraction" of an arm unit.

FIG. 10A shows whether or not the traveling rotation and revolution of the rear wheel units 12R can be performed in a case in which the rear wheel units 12R are in the state of FIG. 7. That is, since both the front operating portion 109F and the rear operating portion 109R of each brake pedal 109 are not operated to be pushed in this case, both the traveling rotation and revolution of the rear wheel units 12R can be performed. Accordingly, under this situation, the radiation-irradiation device 1 can be made to normally travel and can travel in a small radius through the appropriate revolution of the rear wheel units 12R. The state of the brake pedal 109 in this case is one example of a third state of the invention.

Further, FIG. 10B shows whether or not the traveling rotation and revolution of the rear wheel units 12R can be performed in a case in which the rear wheel units 12R are in the state of FIG. 8. That is, since the front operating portion 109F of each brake pedal 109 is operated to be pushed in this case (the first state of the brake pedal 109), the traveling rotation of the rear wheel units 12R cannot be performed and the revolution of the rear wheel units 12R can be performed. Accordingly, for example, in a case in which the position of the radiation-irradiation device 1 is desired to be finely adjusted at the time of taking of a radiation image, only one of the two rear wheel units 12R is made to be not capable of traveling and rotating (that is, the other rear wheel unit 12R is made to be in the state of FIG. 10A) and the radiation-irradiation device 1 is made to be rotationally moved about the revolution axis AX7 (see FIG. 7 and the like) of the rear wheel unit 12R on the device-placement surface 2 as a whole. Therefore, the position of the radiation-irradiation device 1 can be adjusted. Further, since the traveling rotation of one rear wheel unit 12R, which serves as the axis of rotational movement, cannot be performed during the adjustment of the position of the radiation-irradiation device 1, the shift of the axis of rotational movement, which is caused by the rotation of the rear wheel unit 12R, is prevented.

Since the centroid of the radiation-irradiation device 1 is present considerably close to the front side (+y direction in FIG. 1) in a case in which the radiation-irradiation device 1 is made to travel in a state in which the arm unit 30 elongates, that is, a state shown in FIG. 4, the device is likely to be shaken in a case in which the position of the radiation-irradiation device 1 is to be adjusted. However, in a case in which the radiation-irradiation device 1 is rotationally moved about one rear wheel unit 12R as an axis as described above, the position of the radiation-irradiation device 1 can be adjusted while the shake of the device is prevented and the radiation-irradiation device 1 is stably kept.

In addition, in a case in which the traveling rotation of the rear wheel units 12R cannot be performed regardless of whether or not the position of the radiation-irradiation device 1 is adjusted as described above, incorrect imaging, which is caused by the movement of the radiation-irradiation device 1 at the time of taking of a radiation image, is prevented.

Furthermore, FIG. 10C shows whether or not the traveling rotation and revolution of the rear wheel units 12R can be performed in a case in which the rear wheel units 12R are in the state of FIG. 9. That is, since the rear operating portion 109R of each brake pedal 109 is operated to be pushed in this case (the second state of the brake pedal 109), the traveling rotation of the rear wheel units 12R can be performed and the revolution of the rear wheel units 12R cannot be performed. Accordingly, for example, in a case in which the radiation-irradiation device 1 is desired to be made to travel straight, the brake pedals 109 are made to be in this state while the radiation-irradiation device 1 travels straight. Therefore, it is possible to prevent the wobble of the radiation-irradiation device 1 in the traveling direction caused by the revolution of the rear wheel units 12R and to maintain the straight travel of the radiation-irradiation device 1.

As apparent from the above description, in this embodiment, the front operating portion 109F of the brake pedal 109, the shaft 108, the gear 107, the cam 106, the rod 104, the lever 105, and the disc 103 form first locking means for restraining the traveling rotation of the rear wheel unit 12R, and the rear operating portion 109R of the brake pedal 109, the shaft 108, the gear 107, and the cam 106 form second locking means for restraining the revolution of the rear wheel unit 12R.

Second Embodiment

Figure 11A:
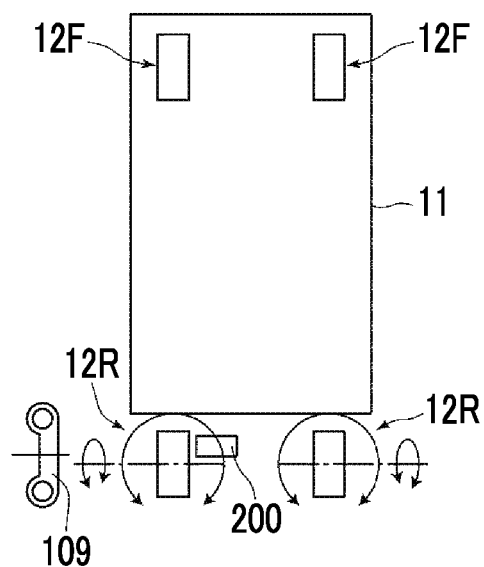
FIGS. 11A, 11B, and 11C are diagrams illustrating the operating states of rear wheels of a radiation-irradiation device according to a second embodiment of the invention.
Figure 11B:
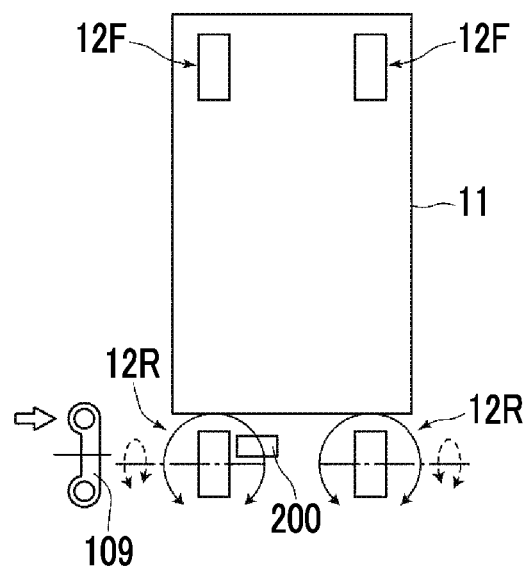
Figure 11C:
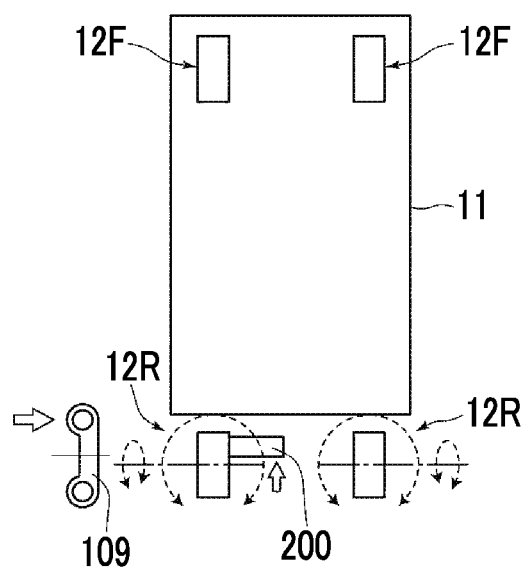

Next, a second embodiment of the invention will be described with reference to FIGS. 11A, 11B, and 11C. FIGS. 11A, 11B, and 11C illustrate whether or not the traveling rotation and revolution of rear wheel units 12R of this embodiment can be performed, and ways to show whether or not the traveling rotation and revolution of the rear wheel units 12R of this embodiment can be performed in FIGS. 11A, 11B, and 11C are the same as those of FIGS. 10A, 10B, and 10C.

The second embodiment is different from the above-mentioned first embodiment in terms of second locking means for restraining the revolution of the rear wheel unit 12R, and others of the second embodiment have basically the same structure as those of the first embodiment. That is, in this embodiment, a seesaw-like brake pedal 200 is mounted on the base 11 at a portion close to a rear end portion (a lower end portion in FIGS. 11A, 11B, and 11C) of the base 11. The brake pedal 200 as the second locking means is provided for each of the two rear wheel units 12R, but only one brake pedal 200 is shown in FIGS. 11A, 11B, and 11C as in the case of the brake pedal 109.

The brake pedal 200 is operated in the form of a seesaw so as to take an oscillating position where one end portion of the brake pedal 200 is in pressure contact with the cylindrical portion 101a (see FIGS. 7 to 9) of the casing 101 of the rear wheel unit 12R and an oscillating position where one end portion of the brake pedal 200 is away from the cylindrical portion 101a.

FIG. 11A shows whether or not the traveling rotation and revolution of the rear wheel units 12R can be performed in a case in which the rear wheel units 12R are in the state of FIG. 7 and the brake pedals 200 take the oscillating position where one end portion of the brake pedal 200 is away from the cylindrical portion 101a of the casing 101. That is, since both the front operating portion 109F and the rear operating portion 109R of each brake pedal 109 are not operated to be pushed and each brake pedal 200 is also not operated to press the cylindrical portion 101a of the casing 101 in this case, both the traveling rotation and revolution of the rear wheel units 12R can be performed. Accordingly, under this situation, the radiation-irradiation device 1 can be made to normally travel and can travel in a small radius through the appropriate revolution of the rear wheel units 12R.

Further, FIG. 11B shows whether or not the traveling rotation and revolution of the rear wheel units 12R can be performed in a case in which the rear wheel units 12R are in the state of FIG. 8 and the brake pedals 200 take the oscillating position where one end portion of the brake pedal 200 is away from the cylindrical portion 101a of the casing 101. That is, since the front operating portion 109F of each brake pedal 109 is operated to be pushed and each brake pedal 200 does not press the cylindrical portion 101a of the casing 101 in this case, the traveling rotation of the rear wheel units 12R cannot be performed and the revolution of the rear wheel units 12R can be performed. Accordingly, for example, in a case in which the position of the radiation-irradiation device 1 is desired to be finely adjusted at the time of taking of a radiation image, only one of the two rear wheel units 12R is made to be not capable of traveling and rotating and the radiation-irradiation device 1 is made to be rotationally moved about the revolution axis AX7 of the rear wheel unit 12R on the device-placement surface 2 as a whole. Therefore, the position of the radiation-irradiation device 1 can be adjusted. Further, since the traveling rotation of one rear wheel unit 12R, which serves as the axis of rotational movement, cannot be performed during the adjustment of the position of the radiation-irradiation device 1, the shift of the axis of rotational movement, which is caused by the rotation of the rear wheel unit 12R, is prevented. In addition, in a case in which the traveling rotation of the rear wheel units 12R cannot be performed regardless of whether or not the position of the radiation-irradiation device 1 is adjusted in this way, incorrect imaging, which is caused by the movement of the radiation-irradiation device 1 at the time of taking of a radiation image, is prevented.

Furthermore, FIG. 11C shows whether or not the traveling rotation and revolution of the rear wheel units 12R can be performed in a case in which the rear wheel units 12R are in the state of FIG. 8 and the brake pedals 200 take the oscillating position where one end portion of the brake pedal 200 presses the cylindrical portion 101a of the casing 101. That is, since the front operating portion 109F of each brake pedal 109 is operated to be pushed and each brake pedal 200 presses the cylindrical portion 101a of the casing 101 in this case, both the traveling rotation and revolution of the rear wheel units 12R cannot be performed.

Accordingly, for example, in a case in which the radiation-irradiation device 1 is desired to be made to travel straight, the brake pedals 200 are operated to be pushed while the radiation-irradiation device 1 travels straight. Therefore, it is possible to prevent the wobble of the radiation-irradiation device 1 in the traveling direction caused by the revolution of the rear wheel units 12R and to maintain the straight travel of the radiation-irradiation device 1. Further, in a case in which the radiation-irradiation device 1 reaches an appropriate position to take, for example, a radiation image and the front operating portions 109F of the brake pedals 109 are operated to be pushed to restrain the traveling rotation of the rear wheel units 12R, incorrect imaging, which is caused by the movement of the radiation-irradiation device 1, is prevented.

As apparent from the above description, in this embodiment, the front operating portion 109F of the brake pedal 109, the shaft 108, the gear 107, the cam 106, the rod 104, the lever 105, and the disc 103 (see FIGS. 6 and 7) form first locking means for restraining the traveling rotation of the rear wheel unit 12R, and the brake pedal 200 forms second locking means for restraining the revolution of the rear wheel unit 12R.

Third Embodiment

Figure 12:
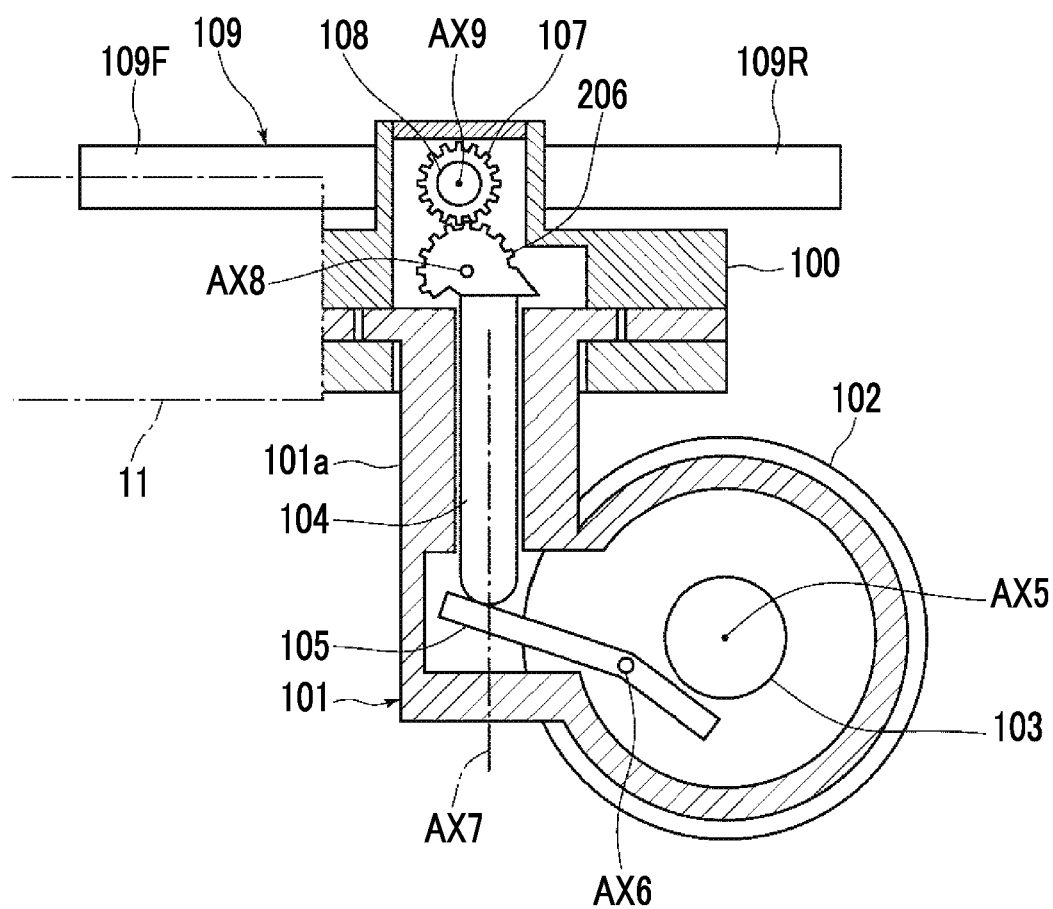
FIG. 12 is a partial cross-sectional side view of a rear wheel of a radiation-irradiation device according to a third embodiment of the invention.

Next, a third embodiment of the invention will be described with reference to FIGS. 12 to 15. FIG. 12 is a partial cross-sectional side view showing the internal structure of a rear wheel unit 12R of this embodiment. The internal structure of the rear wheel unit 12R shown in FIG.

12 is different from the structure of the rear wheel unit of the first embodiment shown in FIG. 7 in that a cam 206 having a shape different from the shape of the cam 106 is applied instead of the cam 106.

Figure 13:
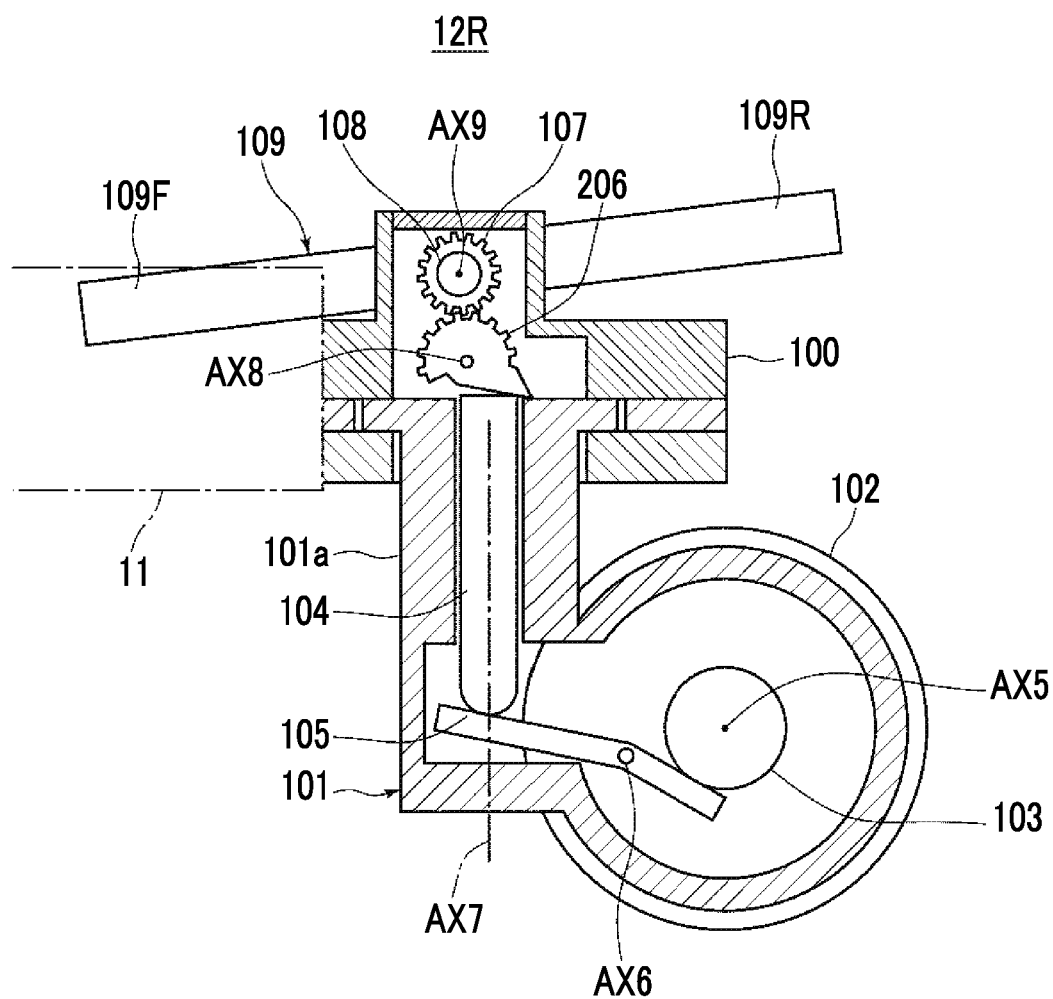
FIG. 13 is a partial cross-sectional side view showing that the rear wheel shown in FIG. 12 is in another state.

In a case in which the front operating portion 109F of the brake pedal 109 as a locking-operating part for one wheel is operated to be pushed down in the rear wheel unit 12R having the above-mentioned structure, an operating force is transmitted to the cam 206 through the shaft 108 and the cam 206 is rotationally moved about the rotational movement axis AX8 in the clockwise direction in FIG. 12. A state in this case is shown in FIG. 13. As shown in FIG. 13, the cam 206, which has been rotationally moved, pushes the rod 104 down against the above-mentioned biasing force. Accordingly, since one end portion of the lever 105 is pushed by the rod 104, the lever 105 oscillates about the oscillation axis AX6 in a counterclockwise direction in FIG. 13. Therefore, the other end portion of the lever 105 presses the disc 103, so that the rotation of the disc 103, that is, the traveling rotation of the wheel 102 is restrained. Further, the cam 206, which has been rotationally moved as described above, presses the upper end face of the cylindrical portion 101a of the casing 101. Accordingly, the revolution of the casing 101 is restrained, so that the revolution of the wheels 102 of the rear wheel unit 12R is restrained. The state of the brake pedal 109, which restrains the traveling rotation and revolution of the rear wheel unit 12R as described above, is one example of the first state of the invention.

Figure 14:
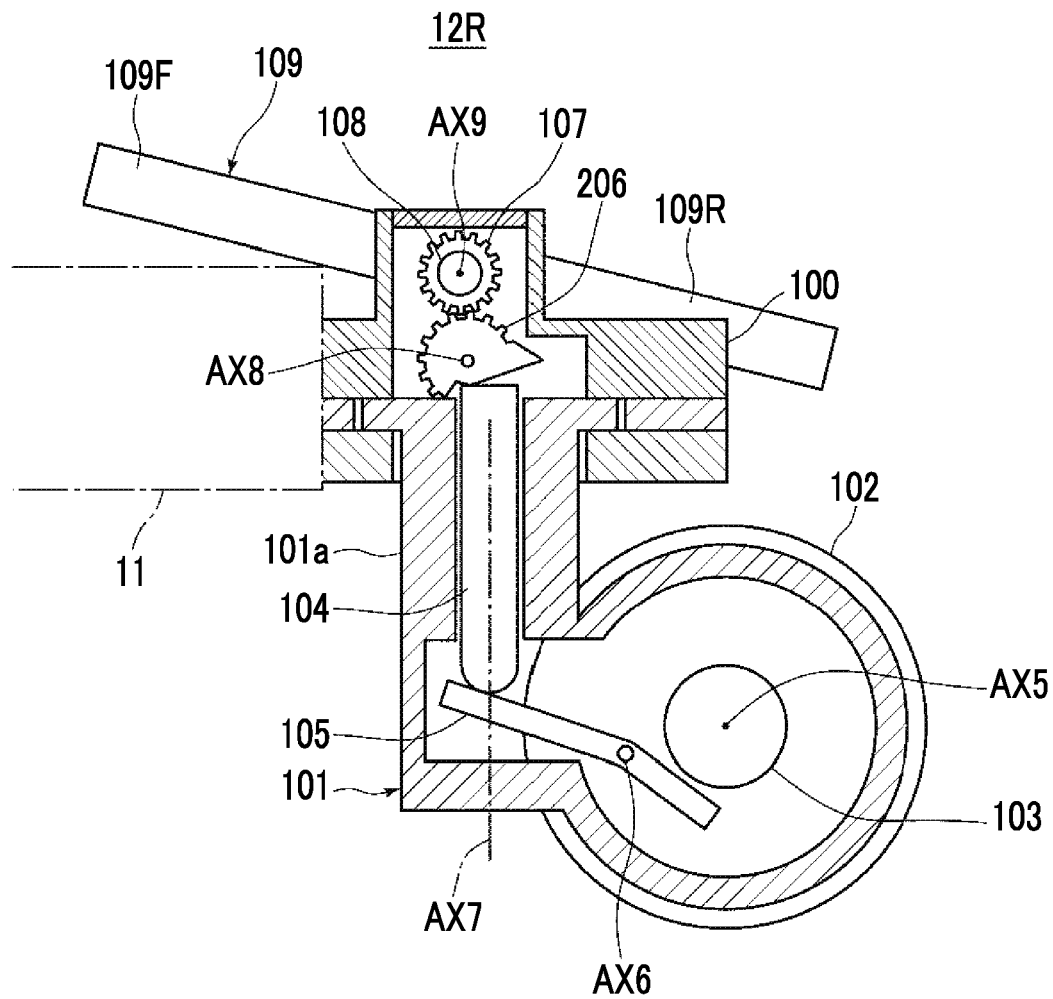
FIG. 14 is a partial cross-sectional side view showing that the rear wheel shown in FIG. 12 is in still another state.

On the other hand, in a case in which the rear operating portion 109R of the brake pedal 109 is operated to be pushed down, an operating force is transmitted to the cam 206 through the shaft 108 and the cam 206 is rotationally moved about the rotational movement axis AX8 in the counter-clockwise direction in FIG. 12. A state in this case is shown in FIG. 14. As shown in FIG. 14, the cam 206, which has been rotationally moved, presses the upper end face of the cylindrical portion 101a of the casing 101. Accordingly, the revolution of the casing 101 is restrained, so that the revolution of the wheels 102 of the rear wheel unit 12R is restrained. The state of the brake pedal 109, which restrains the revolution of the rear wheel unit 12R as described above, is one example of the second state of the invention.

Figure 15A:
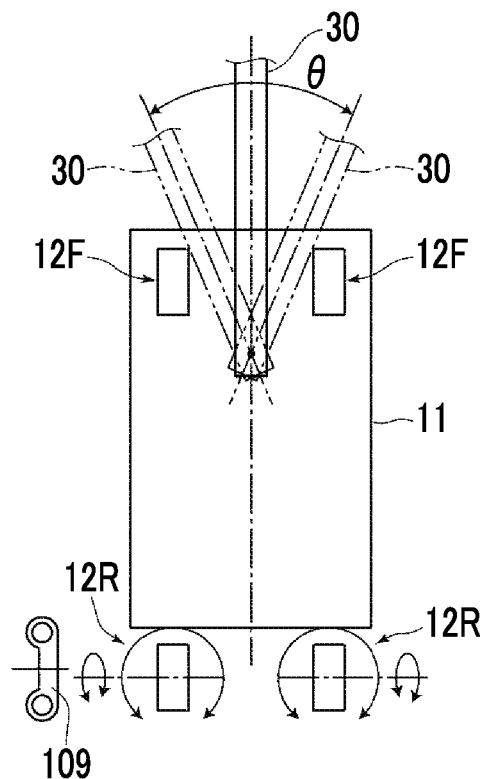
FIGS. 15A, 15B, and 15C are diagrams illustrating the operating states of the rear wheels of the radiation-irradiation device according to the third embodiment of the invention.
Figure 15B:
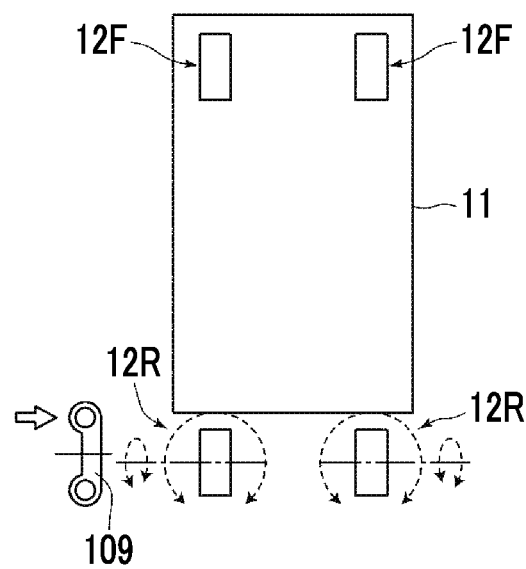
Figure 15C:
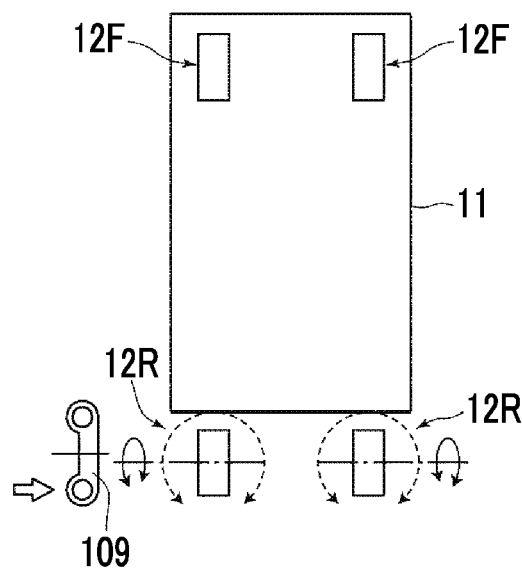

The first and second states having been described above will be described in detail with reference to FIGS. 15A, 15B, and 15C. FIGS. 15A, 15B, and 15C show whether or not the traveling rotation and revolution of the rear wheel units 12R can be performed, and ways to show whether or not the traveling rotation and revolution of the rear wheel units 12R can be performed in FIGS. 15A, 15B, and 15C are the same as those of FIGS. 10A, 10B, and 10C.

FIG. 15A shows whether or not the traveling rotation and revolution of the rear wheel units 12R can be performed in a case in which the rear wheel units 12R are in the state of FIG. 12. That is, since both the front operating portion 109F and the rear operating portion 109R of each brake pedal 109 are not operated to be pushed in this case, both the traveling rotation and revolution of the rear wheel units 12R can be performed. The state of the brake pedal 109 in this case is one example of the third state of the invention. Accordingly, under this situation, the radiation-irradiation device 1 can be made to normally travel and can travel in a small radius through the appropriate revolution of the rear wheel units 12R.

Further, FIG. 15B shows whether or not the traveling rotation and revolution of the rear wheel units 12R can be performed in a case in which the rear wheel units 12R are in the state of FIG. 13. That is, since the front operating portion 109F of each brake pedal 109 is operated to be pushed in this case (the first state of the brake pedal 109), the traveling rotation of the rear wheel units 12R cannot be performed and the revolution of the rear wheel units 12R can be performed.

Furthermore, FIG. 15C shows whether or not the traveling rotation and revolution of the rear wheel units 12R can be performed in a case in which the rear wheel units 12R are in the state of FIG. 14. That is, since the rear operating portion 109R of each brake pedal 109 is operated to be pushed in this case (the second state of the brake pedal 109), the traveling rotation of the rear wheel units 12R can be performed and the revolution of the rear wheel units 12R cannot be performed.

Accordingly, for example, in a case in which the radiation-irradiation device 1 is desired to be made to travel straight, the rear operating portions 109R of the brake pedals 109 are operated to be pushed while the radiation-irradiation device 1 travels straight. Therefore, the rear wheel units 12R are in the state of FIG. 15C in which the revolution of the rear wheel units 12R is restrained. As a result, it is possible to prevent the wobble of the radiation-irradiation device 1 in the traveling direction caused by the revolution of the rear wheel units 12R and to maintain the straight travel of the radiation-irradiation device 1. Further, in a case in which the radiation-irradiation device 1 reaches an appropriate position to take, for example, a radiation image, the front operating portions 109F of the brake pedals 109 are operated to be pushed to make the rear wheel units 12R be in the state of FIG. 15B in which the traveling rotation and revolution of the rear wheel units 12R are restrained. In a case in which the rear wheel units 12R are in this state, incorrect imaging, which is caused by the movement of the radiation-irradiation device 1, is prevented.

As apparent from the above description, in this embodiment, the front operating portion 109F of the brake pedal 109, the shaft 108, the gear 107, the cam 206, the rod 104, the lever 105, and the disc 103 form first locking means for restraining the traveling rotation of the rear wheel unit 12R, and the rear operating portion 109R of the brake pedal 109, the shaft 108, the gear 107, and the cam 206 form second locking means for restraining the revolution of the rear wheel unit 12R.

Fourth Embodiment

Figure 16:
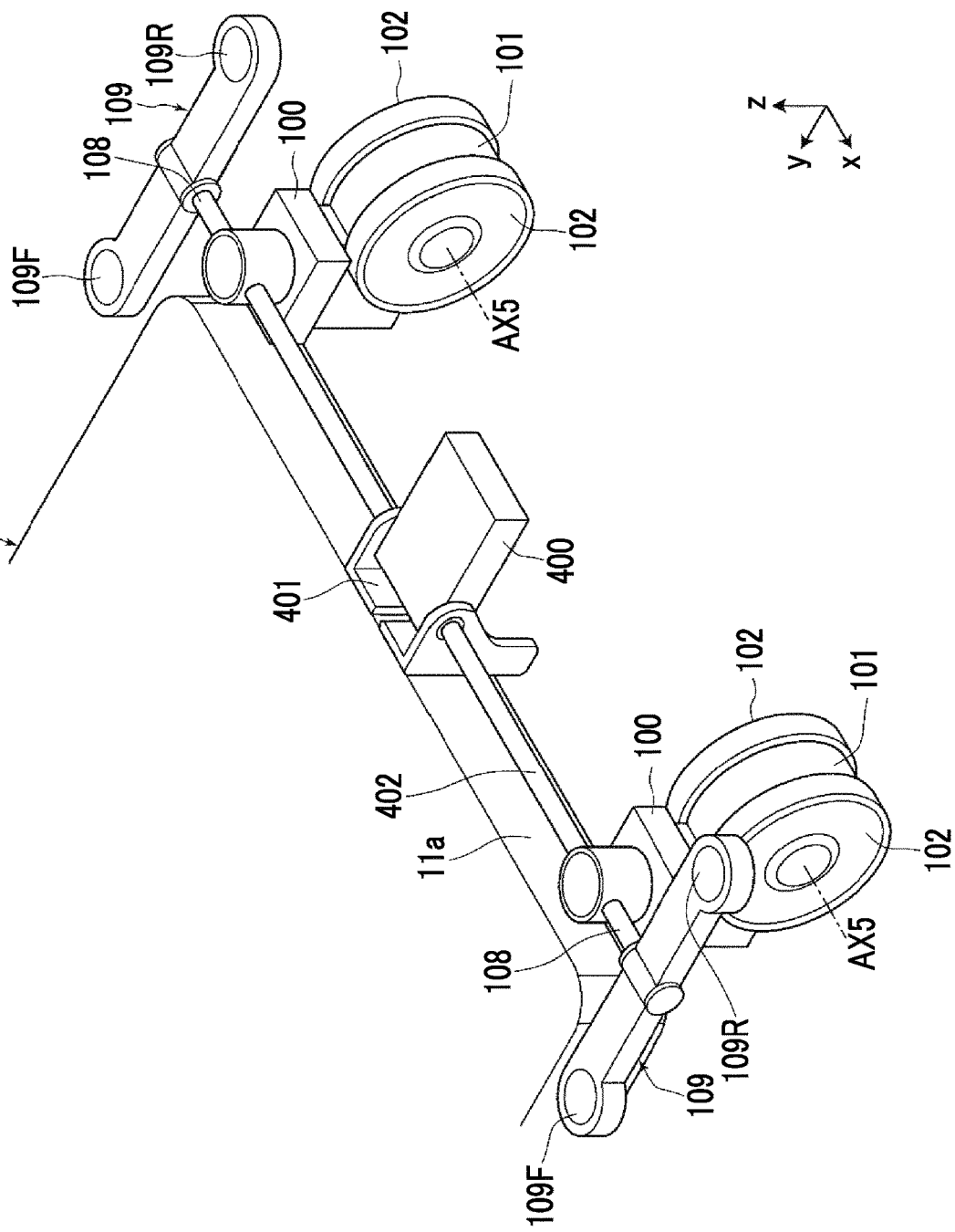
FIG. 16 is a perspective view showing peripheral portions of rear wheels of a radiation-irradiation device according to a fourth embodiment of the invention.

Next, a fourth embodiment of the invention will be described with reference to FIG. 16 and FIGS. 17A, 17B, and 17C. FIG. 16 is a perspective view showing peripheral portions of rear wheels of a radiation-irradiation device according to a fourth embodiment of the invention. The internal structure of the rear wheel unit 12R shown in FIG. 16 is different from the structure of the rear wheel unit of the first embodiment shown in FIG. 6 in that a brake pedal 400 for two wheels as a locking-operating part for a plurality of wheels, a holding member 401 holding the brake pedal 400 for two wheels on, for example, a rear end face 11a of the base 11, and a brake shaft 402 are provided. One end and the other end of the brake shaft 402 are connected to shafts 108 of two rear wheel units 12R, respectively. Further, the brake pedal 400 for two wheels is fixed to the middle portion of the brake shaft 402.

Further, in this embodiment, a rear wheel unit, of which the traveling rotation is restrained in a case in which the rear operating portion 109R (for example, see FIG. 7) of the brake pedal 109 is operated to be pushed and the revolution is restrained in a case in which the front operating portion 109F (for example, see FIG. 7) of the brake pedal 109 is operated to be pushed, is applied as the rear wheel unit 12R. The structure of this rear wheel unit can be realized in a case in which another additional gear is interposed between the cam 106 and the gear 107 in the structure shown FIG. 7. Furthermore, the brake pedal 400 for two wheels is adapted to be capable of being pushed down, and an operating force is transmitted to the shafts 108 of the two rear wheel units 12R through the brake shaft 402 in a case in which the brake pedal 400 for two wheels is operated to be pushed down. That is, the same state as a state in which the rear operating portions 109R of the two rear wheel units 12R are simultaneously operated to be pushed is made in a case in which the brake pedal 400 for two wheels is operated to be pushed down.

Figure 17A:
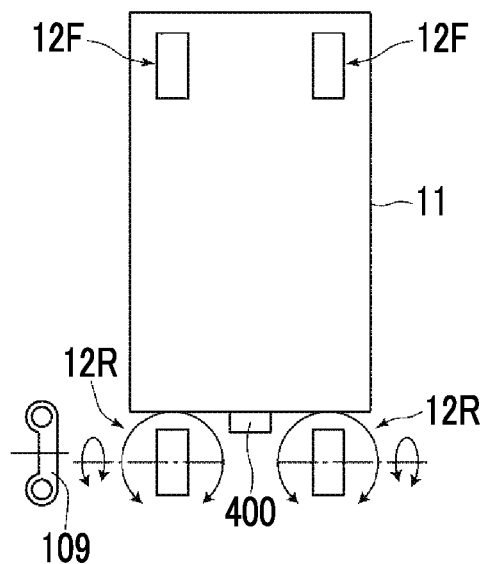
FIGS. 17A, 17B, and 17C are diagrams illustrating the operating states of the rear wheels of the radiation-irradiation device according to the fourth embodiment.
Figure 17B:
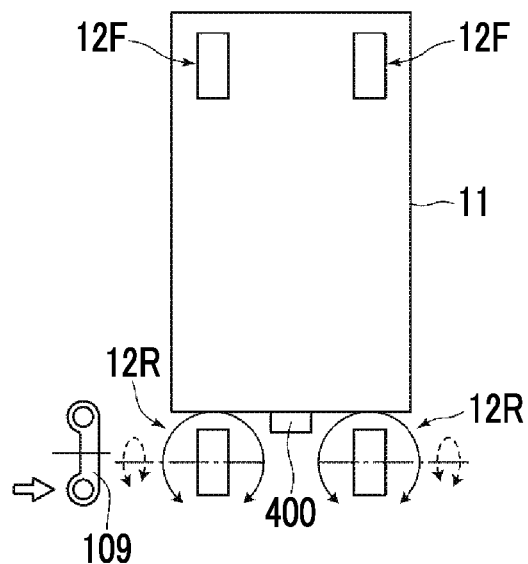
Figure 17C:
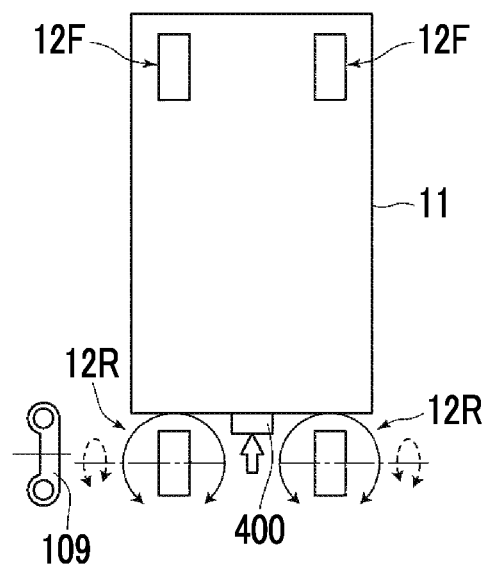

Whether or not the traveling rotation and revolution of the rear wheel units 12R of this embodiment can be performed will be described with reference to FIGS. 17A, 17B, and 17C. Ways to show whether or not the traveling rotation and revolution of the rear wheel units 12R can be performed in FIGS. 17A, 17B, and 17C are the same as those of FIGS. 10A, 10B, and 10C. Further, the operation state of the brake pedal 400 for two wheels is shown in FIGS. 17A, 17B, and 17C together, and the fact that an outline arrow is shown below the brake pedal 400 for two wheels in FIGS. 17A, 17B, and 17C means that the brake pedal 400 for two wheels is operated to be pushed.

FIG. 17A shows whether or not the traveling rotation and revolution of the rear wheel units 12R can be performed in a case in which the rear operating portions 109R of the brake pedals 109 and the brake pedal 400 for two wheels are not operated to be pushed. In this case, both the traveling rotation and revolution of the rear wheel units 12R can be performed. Accordingly, under this situation, the radiation-irradiation device 1 can be made to normally travel and can travel in a small radius through the appropriate revolution of the rear wheel units 12R.

Further, FIG. 17B shows whether or not the traveling rotation and revolution of the rear wheel units 12R can be performed in a case in which the rear operating portions 109R of the brake pedals 109 are operated to be pushed. In this case, the traveling rotation of the rear wheel units 12R cannot be performed and the revolution of the rear wheel units 12R can be performed. The operation for pushing the rear operating portion 109R can be performed on the two rear wheel units 12R or can also be performed on only one rear wheel unit 12R. Accordingly, for example, in a case in which the position of the radiation-irradiation device 1 is desired to be finely adjusted at the time of taking of a radiation image, only one of the two rear wheel units 12R is made to be not capable of traveling and rotating and the radiation-irradiation device 1 is made to be rotationally moved about the revolution axis AX7 of the rear wheel unit 12R on the device-placement surface 2 as a whole. Therefore, the position of the radiation-irradiation device 1 can be adjusted.

Further, in a case in which the radiation-irradiation device 1 is desired not to be rotationally moved and the traveling rotation of both the two rear wheel units 12R is desired not to be capable of being performed, the brake pedal 400 for two wheels is operated to be pushed as shown in FIG. 17C. Accordingly, it is possible to more quickly restrain the traveling rotation of the two rear wheel units 12R than a case in which the respective brake pedals 109 of the two rear wheel units 12R are operated to be pushed.

Although not shown in FIGS. 17A, 17B, and 17C, the traveling rotation of the rear wheel units 12R can be performed and the revolution of the rear wheel units 12R cannot be performed in a case in which the front operating portions 109F of the brake pedals 109 are operated to be pushed. For example, in a case in which the radiation-irradiation device 1 is desired to be made to travel straight, the two rear wheel units 12R are made to be in this state while the radiation-irradiation device 1 travels straight. Accordingly, it is possible to prevent the wobble of the radiation-irradiation device 1 in the traveling direction caused by the revolution of the rear wheel units 12R and to maintain the straight travel of the radiation-irradiation device 1.

As apparent from the above description, in this embodiment, in a case in which the above-mentioned additional gear is applied to the rear operating portion 109R of the brake pedal 109, the shaft 108, the gear 107, the cam 106, the rod 104, the lever 105, and the disc 103 (see FIGS. 6 and 7), the structure to which the additional gear is added and a structure in which the rear operating portions 109R of the brake pedals 109 are substituted with the brake pedal 400 for two wheels and the brake shaft 402 in the above-mentioned structure form first locking means for restraining the traveling rotation of the rear wheel units 12R. Further, in a case in which the above-mentioned additional gear is applied to the front operating portion 109F of the brake pedal 109, the shaft 108, the gear 107, and the cam 106 (see FIGS. 6 and 7), the structure to which the additional gear is added forms second locking means for restraining the revolution of the rear wheel unit 12R.

Fifth Embodiment

Figure 18A:
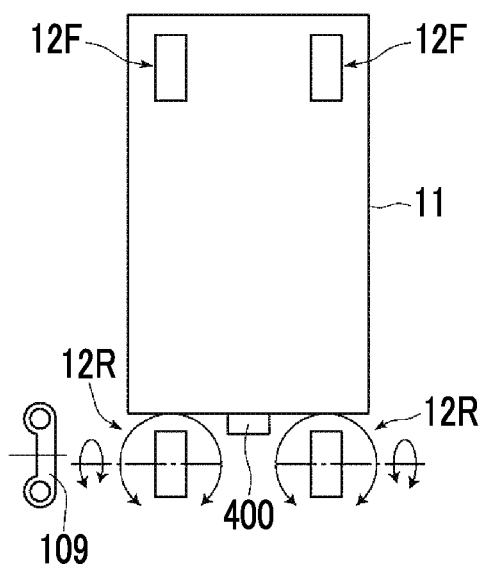
FIGS. 18A, 18B, and 18C are diagrams illustrating the operating states of rear wheels of the radiation-irradiation device according to a fifth embodiment of the invention.
Figure 18B:
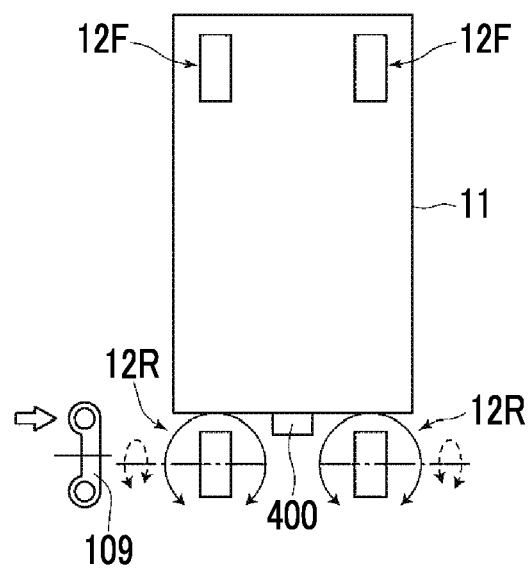
Figure 18C:
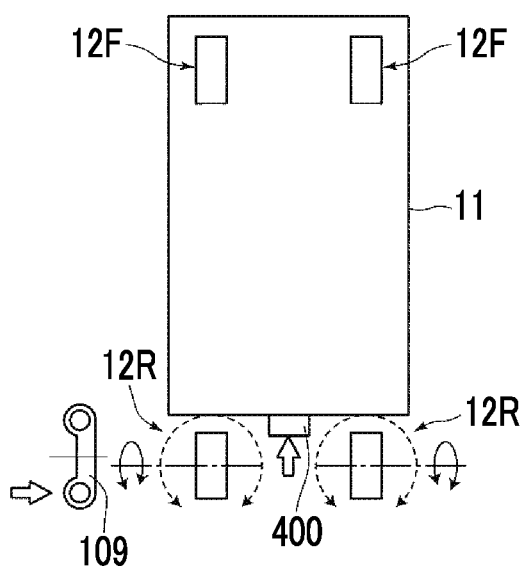

Next, a fifth embodiment of the invention will be described with reference to FIGS. 18A, 18B, and 18C. FIGS. 18A, 18B, and 18C show whether or not the traveling rotation and revolution of rear wheel units 12R of this embodiment can be performed, and ways to show whether or not the traveling rotation and revolution of the rear wheel units 12R of this embodiment can be performed in FIGS. 18A, 18B, and 18C are the same as those of FIGS. 10A, 10B, and 10C.

A brake pedal 400 for two wheels, a holding member 401, and a brake shaft 402, which are the same as those shown in FIG. 16, are provided in this embodiment. FIGS. 18A, 18B, and 18C show the operation states of the brake pedal 400 for two wheels by the same ways to show the operation states as those of FIGS. 17A, 17B, and 17C. Further, the same rear wheel unit 12R as that shown in FIGS. 7 to 9 is applied as each of the two rear wheel units 12R in this embodiment. In a case in which the brake pedal 400 for two wheels is operated to be pushed in the above-mentioned structure, each rear wheel unit 12R is in the same state as the state in which the rear operating portion 109R of the brake pedal 109 is operated to be pushed as shown in FIG. 9.

FIG. 18A shows whether or not the traveling rotation and revolution of the rear wheel units 12R can be performed in a case in which the rear wheel units 12R are in the state of FIG. 7. That is, since both the front operating portion 109F and the rear operating portion 109R of each brake pedal 109 are not operated to be pushed (the third state of the brake pedal 109) and the brake pedal 400 for two wheels is also not operated to be pushed in this case, both the traveling rotation and revolution of the rear wheel units 12R can be performed. Accordingly, under this situation, the radiation-irradiation device 1 can be made to normally travel and can travel in a small radius through the appropriate revolution of the rear wheel units 12R.

Further, FIG. 18B shows whether or not the traveling rotation and revolution of the rear wheel units 12R can be performed in a case in which the rear wheel units 12R are in the state of FIG. 8. That is, since the front operating portion 109F of each brake pedal 109 is operated to be pushed in this case (the first state of the brake pedal 109), the traveling rotation of the rear wheel units 12R cannot be performed and the revolution of the rear wheel units 12R can be performed. Accordingly, for example, in a case in which the position of the radiation-irradiation device 1 is desired to be finely adjusted at the time of taking of a radiation image, only one of the two rear wheel units 12R is made to be not capable of traveling and rotating and the radiation-irradiation device 1 is made to be rotationally moved about the revolution axis AX7 of the rear wheel unit 12R on the device-placement surface 2 as a whole. Therefore, the position of the radiation-irradiation device 1 can be adjusted. Further, in a case in which the traveling rotation of the rear wheel units 12R is made to be not capable of being performed regardless of whether or not the position of the radiation-irradiation device 1 is adjusted as described above, incorrect imaging, which is caused by the movement of the radiation-irradiation device 1 at the time of taking of a radiation image, is prevented.

Furthermore, FIG. 18C shows whether or not the traveling rotation and revolution of the rear wheel units 12R can be performed in a case in which the rear wheel units 12R are in the state of FIG. 9. That is, since the rear operating portions 109R of the respective brake pedals 109 of the two rear wheel units 12R are operated to be pushed (the second state of the brake pedal 109) or the brake pedal 400 for two wheels is operated to be pushed in this case, the traveling rotation of the rear wheel units 12R can be performed and the revolution of the rear wheel units 12R cannot be performed. Accordingly, for example, in a case in which the radiation-irradiation device 1 is desired to be made to travel straight, the brake pedals 109 are made to be in this state while the radiation-irradiation device 1 travels straight. Therefore, it is possible to prevent the wobble of the radiation-irradiation device 1 in the traveling direction caused by the revolution of the rear wheel units 12R and to maintain the straight travel of the radiation-irradiation device 1.

In a case in which the brake pedal 400 for two wheels is to be operated to be pushed to make the state of FIG. 18C, a brake operation only has to be performed one time. That is, in this case, a brake operation is easier than a case in which the rear operating portions 109R of the respective brake pedals 109 of the two rear wheel units 12R are operated to be pushed. Further, the operation for pushing the brake pedal 400 for two wheels can also be performed while the radiation-irradiation device 1 is made to travel and is transported. In this case, a brake operation is more quickly performed than a case in which the rear operating portions 109R of the respective brake pedals 109 of the two rear wheel units 12R are operated to be pushed. Accordingly, it is particularly preferable that the brake pedal 400 for two wheels is applied.

As apparent from the above description, in this embodiment, the front operating portion 109F of the brake pedal 109, the shaft 108, the gear 107, the cam 106, the rod 104, the lever 105, and the disc 103 (see FIGS. 6 and 7) form first locking means for restraining the traveling rotation of the rear wheel unit 12R. Further, the rear operating portion 109R of the brake pedal 109, the shaft 108, the gear 107, and the cam 106 (see FIGS. 6 and 7) form second locking means for restraining the revolution of the rear wheel unit 12R; and the brake pedal 400 for two wheels, the brake shaft 402, the shaft 108, the gear 107, and the cam 106 also form second locking means for restraining the revolution of the rear wheel unit 12R.

Sixth Embodiment

Figure 19A:
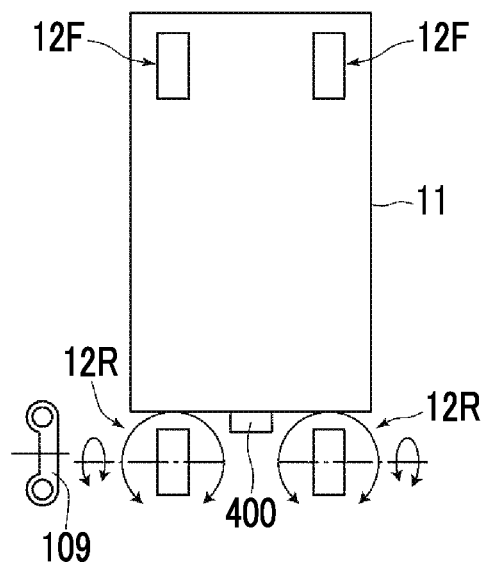
FIGS. 19A, 19B, and 19C are diagrams illustrating the operating states of rear wheels of a radiation-irradiation device according to a sixth embodiment of the invention.
Figure 19B:
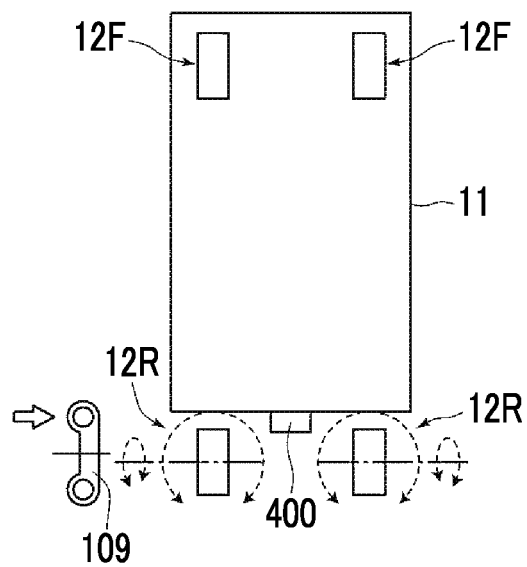
Figure 19C:
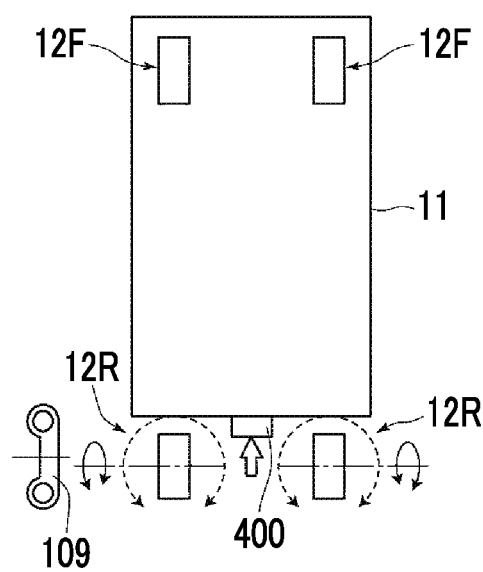

Next, a sixth embodiment of the invention will be described with reference to FIGS. 19A, 19B, and 19C. FIGS. 19A, 19B, and 19C show whether or not the traveling rotation and revolution of rear wheel units 12R of this embodiment can be performed, and ways to show whether or not the traveling rotation and revolution of the rear wheel units 12R of this embodiment can be performed in 19A, 19B, and 19C are the same as those of FIGS. 18A, 18B, and 18C.

A brake pedal 400 for two wheels, a holding member 401, and a brake shaft 402, which are the same as those shown in FIG. 16, are provided in this embodiment. FIGS. 19A, 19B, and 19C show the operation states of the brake pedal 400 for two wheels by the same ways to show the operation states as those of FIGS. 17A, 17B, and 17C. Further, the same rear wheel unit 12R as that shown in FIGS. 12 to 14 is applied as each of the two rear wheel units 12R in this embodiment. In a case in which the brake pedal 400 for two wheels is operated to be pushed in the above-mentioned structure, each rear wheel unit 12R is in the same state as the state in which the rear operating portion 109R of the brake pedal 109 is operated to be pushed as shown in FIG. 14.

FIG. 19A shows whether or not the traveling rotation and revolution of the rear wheel units 12R can be performed in a case in which the rear wheel units 12R are in the state of FIG. 12. That is, since both the front operating portion 109F and the rear operating portion 109R of each brake pedal 109 are not operated to be pushed (the third state of the brake pedal 109) and the brake pedal 400 for two wheels is also not operated to be pushed in this case, both the traveling rotation and revolution of the rear wheel units 12R can be performed. Accordingly, under this situation, the radiation-irradiation device 1 can be made to normally travel and can travel in a small radius through the appropriate revolution of the rear wheel units 12R.

Further, FIG. 19B shows whether or not the traveling rotation and revolution of the rear wheel units 12R can be performed in a case in which the rear wheel units 12R are in the state of FIG. 13. That is, since the front operating portion 109F of each brake pedal 109 is operated to be pushed in this case (the first state of the brake pedal 109), both the traveling rotation and revolution of the rear wheel units 12R cannot be performed.

Making the brake pedal 109 be in the first state as described above can also be performed on both the two rear wheel units 12R or only one of the two rear wheel units 12R. Accordingly, for example, in a case in which the position of the radiation-irradiation device 1 is desired to be finely adjusted at the time of taking of a radiation image, only one of the two rear wheel units 12R is made to be not capable of traveling and rotating and the radiation-irradiation device 1 is made to be rotationally moved about the revolution axis AX7 of the rear wheel unit 12R on the device-placement surface 2 as a whole. Therefore, the position of the radiation-irradiation device 1 can be adjusted. Further, in a case in which the traveling rotation of the two rear wheel units 12R is made to be not capable of being performed regardless of whether or not the position of the radiation-irradiation device 1 is adjusted as described above, incorrect imaging, which is caused by the movement of the radiation-irradiation device 1 at the time of taking of a radiation image, is prevented.

Furthermore, FIG. 19C shows whether or not the traveling rotation and revolution of the rear wheel units 12R can be performed in a case in which the rear wheel units 12R are in the state of FIG. 14. That is, since the rear operating portions 109R of the brake pedals 109 are operated to be pushed (the second state of the brake pedal 109) or the brake pedal 400 for two wheels is operated to be pushed in this case, the traveling rotation of the rear wheel units 12R can be performed and the revolution of the rear wheel units 12R cannot be performed.

Accordingly, for example, in a case in which the radiation-irradiation device 1 is desired to be made to travel straight, the rear operating portions 109R of the brake pedals 109 are operated to be pushed or the brake pedal 400 for two wheels is operated to be pushed while the radiation-irradiation device 1 travels straight. Therefore, the rear wheel units 12R are in the state of FIG. 19C in which the revolution of the rear wheel units 12R is restrained. As a result, it is possible to prevent the wobble of the radiation-irradiation device 1 in the traveling direction caused by the revolution of the rear wheel units 12R and to maintain the straight travel of the radiation-irradiation device 1. Further, in a case in which the radiation-irradiation device 1 reaches an appropriate position to take, for example, a radiation image, the front operating portions 109F of the brake pedals 109 are operated to be pushed to make the rear wheel units 12R be in the state of FIG. 19B in which the traveling rotation and revolution of the rear wheel units 12R are restrained. In a case in which the rear wheel units 12R are in this state, incorrect imaging, which is caused by the movement of the radiation-irradiation device 1, is prevented.

In a case in which the brake pedal 400 for two wheels is to be operated to be pushed to make the state of FIG. 19C, a brake operation only has to be performed one time. That is, in this case, a brake operation is easier than a case in which the rear operating portions 109R of the respective brake pedals 109 of the two rear wheel units 12R are operated to be pushed. Further, the operation for pushing the brake pedal 400 for two wheels can also be performed while the radiation-irradiation device 1 is made to travel and is transported. In this case, a brake operation is more quickly performed than a case in which the rear operating portions 109R of the respective brake pedals 109 of the two rear wheel units 12R are operated to be pushed. Accordingly, it is particularly preferable that the brake pedal 400 for two wheels is applied.

As apparent from the above description, in this embodiment, the front operating portion 109F of the brake pedal 109, the shaft 108, the gear 107, the cam 206, the rod 104, the lever 105, and the disc 103 (see FIGS. 6 and 12) form first locking means for restraining the traveling rotation of the rear wheel unit 12R. Further, the rear operating portion 109R of the brake pedal 109, the shaft 108, the gear 107, and the cam 206 (see FIGS. 6 and 12) form second locking means for restraining the revolution of the rear wheel unit 12R; and the brake pedal 400 for two wheels, the brake shaft 402, the shaft 108, the gear 107, and the cam 206 also form second locking means for restraining the revolution of the rear wheel unit 12R.

Seventh Embodiment

Next, an example other than the rear wheel unit 12R, which is formed of the above-mentioned revolving caster, will be described in regard to a rear wheel that is applied to the radiation-irradiation device 1. A rear wheel shown in FIG. 20 is formed of, for example, OMNI WHEEL (registered trademark). FIG. 20 shows a state in which the OMNI WHEEL 700 forming a rear wheel is mounted on the base 11 of the radiation-irradiation device 1 shown in FIG. 1 through a leg holding portion 712 as an example.

The OMNI WHEEL 700 is one of omnidirectionally moving wheels, and includes a rotating body 702 that is mounted on an axle 701 and is rotatable about a rotation axis AX11 in a normal direction and a reverse direction, and a plurality of rollers 703 that are mounted on the outer peripheral portion of the rotating body 702. For example, a barrel-shaped roller is applied as the roller 703.

In this example, seven rollers 703 are mounted on each of left and right sides of the rotating body 702, that is, a total of fourteen rollers 703 are mounted on the rotating body 702. Each of the seven rollers 703, which are mounted on one side of the left and right sides of the rotating body, is mounted on the rotating body 702 so as to be rotatable about a rotation axis AX12, which extends in a tangential direction of one circle coaxial with the rotation axis AX11, in a normal direction and a reverse direction. The same applies to the seven rollers 703 that are mounted on the other side of the left and right sides of the rotating body. Further, the seven rollers 703, which are mounted on one side of the left and right sides of the rotating body, are disposed at positions that face gaps between the seven rollers 703 that are mounted on the other side of the left and right sides of the rotating body. The OMNI WHEEL 700 having the above-mentioned structure is mounted on each leg holding portion 712 through a bearing part 704 receiving the axle 701.

In the case of the OMNI WHEEL 700, the rotating body 702 serving as a wheel body and the fourteen rollers 703 serving as a traveling direction-changing part form one rotating wheel. That is, in a case in which a force acting in the direction of an arrow P of FIG. 20 is applied to the radiation-irradiation device including the leg holding portions 712, each wheel, which includes the rotating body 702 and the rollers 703, rotates about the rotation axis AX11 while the fourteen rollers 703 serve as the outer peripheral surface of each wheel. Accordingly, the leg holding portions 712, that is, the radiation-irradiation device is made to travel in the direction of the arrow P. Further, in a case in which a force acting in the direction of an arrow Q of FIG. 20 is applied to the radiation-irradiation device including the leg holding portions 712, each of the grounded rollers 703 rotates about the rotation axis AX12. Accordingly, the movement of the leg holding portions 712, that is, the radiation-irradiation device in the direction of the arrow Q is facilitated.

Even in a case in which the rear wheel is formed of the above-mentioned OMNI WHEEL 700, first locking means for restraining the rotation, that is, the traveling rotation of the rotating body 702 and second locking means for restraining the rotation of the roller 703 can be provided. Further, it is possible to obtain the radiation-irradiation device of the invention by controlling the operations of these locking means.

For example, a mecanum wheel disclosed in JP2013-081659A can also be applied as the omnidirectionally moving wheel other than the above-mentioned OMNI WHEEL 700.

Eighth Embodiment

Figure 21:
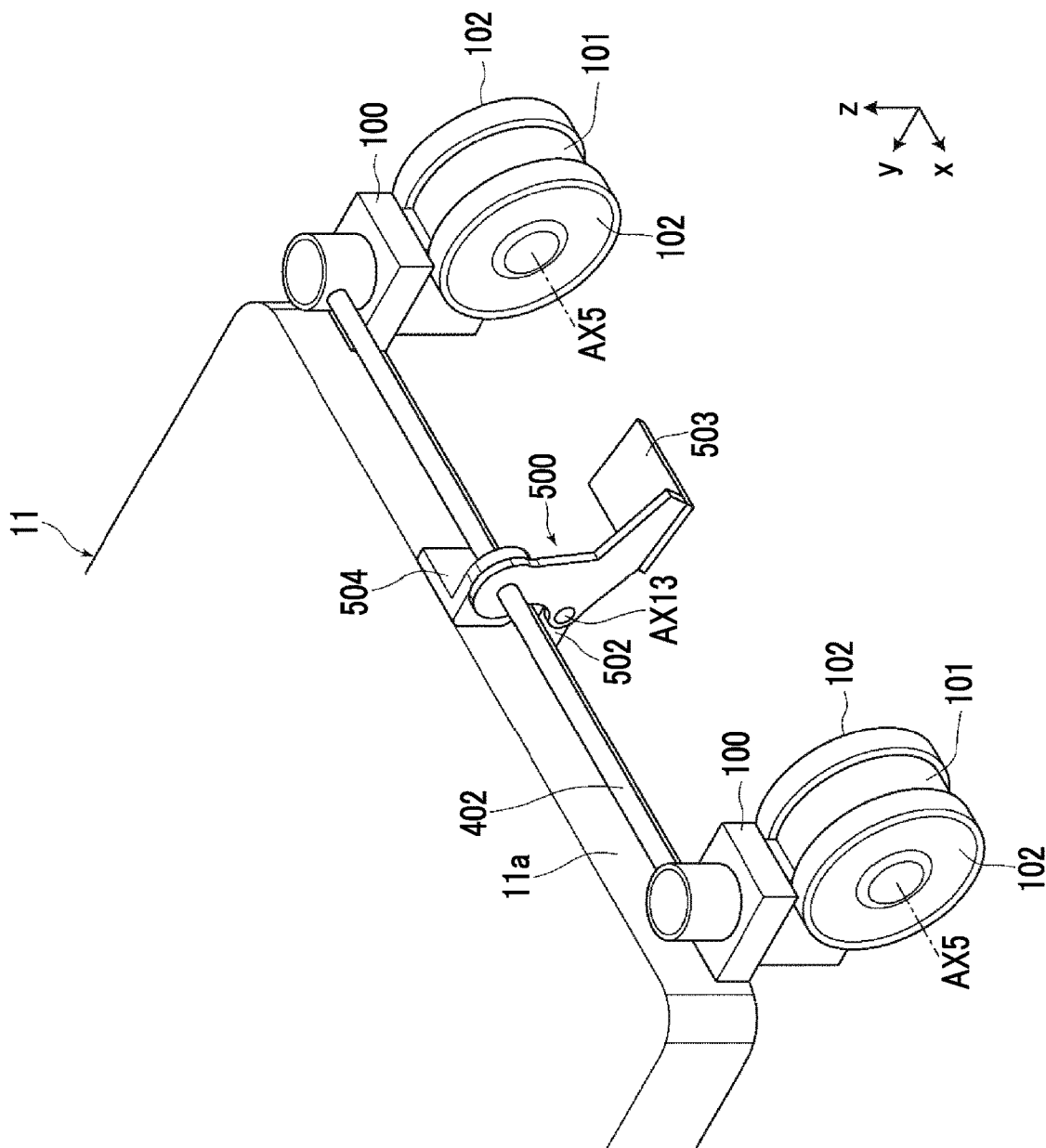
FIG. 21 is a perspective view showing peripheral portions of rear wheels of a radiation-irradiation device according to an eighth embodiment of the invention.

Next, an embodiment in which one locking-operating part is provided with a plurality of operating pieces for operating first and second locking means will be described. FIG. 21 is a perspective view showing peripheral portions of rear wheels of a radiation-irradiation device according to an eighth embodiment of the invention. Further, FIG. 22 is a side view showing a pedal interlocking mechanism that is applied to the radiation-irradiation device according to the eighth embodiment.

Figure 22:
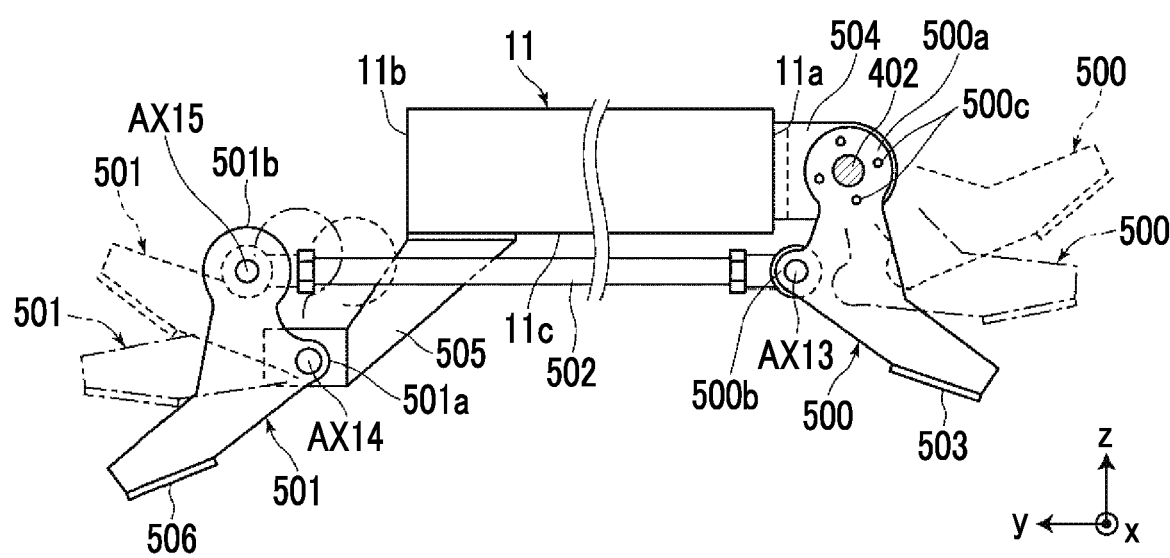
FIG. 22 is a side view showing a pedal interlocking mechanism that is used in the radiation-irradiation device of FIG. 21.

The pedal interlocking mechanism shown in FIG. 22 forms a part of an operating portion for operating the first and second locking means, and includes a rear wheel-side pedal 500 as a rear wheel-side locking-operating piece, a front wheel-side pedal 501 as a front wheel-side locking-operating piece, and a connecting rod 502 that connects the rear wheel-side pedal 500 to the front wheel-side pedal 501. Only the rear wheel-side pedal 500 of the two pedals 500 and 501 is shown in FIG. 21.

As shown in FIG. 22, the rear wheel-side pedal 500 includes a rotating base portion 500a that is provided at an upper end portion (a front end portion in +z direction) thereof and is formed in the shape of a part of a circle, and the rotating base portion 500a is fixed to the brake shaft 402 by, for example, fitting or the like. Accordingly, the rear wheel-side pedal 500 can be rotated integrally with the brake shaft 402. A pedal plate 503 is fixed to a portion of the rear wheel-side pedal 500 close to a lower end. Further, a rod connecting portion 500b, which protrudes toward the front wheel-side pedal 501, is formed on the rear wheel-side pedal 500 at a position close to the vertical middle of the rear wheel-side pedal 500. Further, one end portion of the connecting rod 502 is connected to the rod connecting portion 500b so as to be rotatable about a rotation axis AX13.

A holding member 504 is fixed to the rear end face 11a of the base 11. The holding member 504 includes a through hole (not shown) through which the brake shaft 402 passes, and allows the brake shaft 402 to rotate. The rotating base portion 500a of the rear wheel-side pedal 500 is disposed so as to be in close contact with the holding member 504. The rear wheel-side pedal 500 is disposed on the rear side (a side corresponding to −y direction) of the rear end face 11a of the base 11 in this way.

The rear wheel-side pedal 500, which is rotated integrally with the brake shaft 402, is adapted to be stopped at three rotational positions as described below and to be held at each rotational position. The holding of the rear wheel-side pedal 500 is performed in a case in which a plurality of hemispherical convex portions 500c formed on the rotating base portion 500a is engaged with concave portions (not shown) formed on the holding member 504. In a case in which an external force having a certain magnitude, which allows the rear wheel-side pedal 500 to rotate, is applied to the rear wheel-side pedal 500 that is held at any one of the three rotational positions in this way, the engagement between the convex portions 500c and the concave portions is released and the rear wheel-side pedal 500 can be moved to another rotational position.

The front wheel-side pedal 501 includes a rotating base portion 501a that is provided on the front wheel-side pedal 501 at a position close to the vertical middle of the front wheel-side pedal 501. The rotating base portion 501a is held by a holding member 505, which is fixed to a lower surface 11c of the base 11, so as to be rotatable about a rotation axis AX14. The front wheel-side pedal 501 is disposed on the front side (a side corresponding to +y direction) of a front end face 11b of the base 11 in this way. Further, a rod connecting portion 501b, which is formed in the shape of a part of a circle and protrudes toward the rear wheel-side pedal 500, is formed at an upper end portion (a front end portion in +z direction) of the front wheel-side pedal 501. Furthermore, the other end portion of the connecting rod 502 is connected to the rod connecting portion 501b so as to be rotatable about a rotation axis AX15. Moreover, a pedal plate 506 is fixed to a portion of the front wheel-side pedal 501 close to a lower end.

In the above-mentioned structure, the brake shaft 402 is connected to first and second locking means that are basically the same as those shown in FIG. 12. That is, the shaft 108 shown in FIG. 12 is coaxially connected and fixed to each of one end portion and the other end portion of the brake shaft 402. In this case, the brake pedals 109 shown in FIG. 12 are generally omitted but may be provided. However, in a case in which the brake pedals 109 protrude outside the left and right end faces of the base 11, the brake pedals 109 are likely to interfere with obstacles during the transport of the radiation-irradiation device along a narrow path. Considering that the brake pedals 109 are likely to interfere with obstacles during the transport of the radiation-irradiation device along a narrow path, it is preferable that the brake pedals 109 protruding outside the left and right end faces of the base 11 are omitted.

In a case in which an operator steps on, for example, the pedal plate 503 with a foot, the rear wheel-side pedal 500 can be rotated about the brake shaft 402 in a clockwise direction in FIG. 22. In a case in which an operator raises, for example, the pedal plate 503 from below on tiptoe, the rear wheel-side pedal 500 can be rotated about the brake shaft 402 in a counterclockwise direction in FIG. 22. Further, the rear wheel-side pedal 500 can be held on the above-mentioned path of rotation at a rotational position shown by a solid line, a rotational position shown by a one-dot chain line, and a rotational position shown by a broken line in FIG. 22. Hereinafter, these three rotational positions are referred to as a lower position, a middle position, and an upper position in this order.

For example, in a case in which the rear wheel-side pedal 500 is rotated to the upper position from the lower position, the connecting rod 502 of which one end portion is connected to the rod connecting portion 500b of the rear wheel-side pedal 500 is moved substantially in a right direction in FIG. 22. Accordingly, since the rod connecting portion 501b to which the other end portion of the connecting rod 502 is connected is pulled substantially in the right direction in FIG. 22, the front wheel-side pedal 501 is rotated about the rotation axis AX14 in the clockwise direction. In a case in which the rear wheel-side pedal 500 is set to the lower position, the middle position, and the upper position in this way, the front wheel-side pedal 501 is set to a rotational position shown by a solid line, a rotational position shown by a one-dot chain line, and a rotational position shown by a broken line in FIG. 22. The three rotational positions of the front wheel-side pedal 501 are also referred to as a lower position, a middle position, and an upper position in this order.

In a case in which the rear wheel-side pedal 500 serving as one locking-operating piece is set to the lower position, the middle position, or the upper position as described above, the front wheel-side pedal 501 serving as another locking-operating piece is also set to the lower position, the middle position, or the upper position likewise while interlocking with the rear wheel-side pedal 500. A case in which the front wheel-side pedal 501 is rotationally moved while interlocking with the operation of the rear wheel-side pedal 500 at the time of rotational operation of the rear wheel-side pedal 500 has been described above, but the rear wheel-side pedal 500 may be rotationally moved while interlocking with the operation of the front wheel-side pedal 501 at the time of rotational operation of the front wheel-side pedal 501. That is, the front wheel-side pedal 501 can also be rotated about the rotation axis AX14 and be set to the lower position, the middle position, or the upper position in a case in which the pedal plate 506 is operated as in the case of the pedal plate 503. In this case, the movement of the front wheel-side pedal 501 is transmitted to the rear wheel-side pedal 500 through the connecting rod 502. Accordingly, the rear wheel-side pedal 500 is rotated about the brake shaft 402 and is set to the lower position, the middle position, or the upper position.

In a case in which first and second locking means, which are basically the same as those shown in FIG. 12, are connected to the brake shaft 402 as described above and the rear wheel-side pedal 500 and the front wheel-side pedal 501 are set to the lower positions, the locking means are in the state shown in FIG. 14. That is, in this case, the traveling rotation of the rear wheel units 12R (see FIG. 14) can be performed and the revolution of the rear wheel units 12R cannot be performed. The state of the rear wheel-side pedal 500, which restrains the revolution of the rear wheel units 12R as described above, and the front wheel-side pedal 501 is one example of a second state of the invention.

Further, in a case in which the rear wheel-side pedal 500 and the front wheel-side pedal 501 are set to the middle positions, the locking means are in the state shown in FIG. 12. That is, in this case, both the traveling rotation and revolution of the rear wheel units 12R (see FIG. 12) can be performed.

Further, in a case in which the rear wheel-side pedal 500 and the front wheel-side pedal 501 are set to the upper positions, the locking means are in the state shown in FIG. 13. That is, in this case, both the traveling rotation and revolution of the rear wheel units 12R (see FIG. 13) cannot be performed. The state of the rear wheel-side pedal 500, which restrains the traveling rotation and revolution of the rear wheel units 12R as described above, and the front wheel-side pedal 501 is one example of a first state of the invention.

For example, on the contrary to the example, the radiation-irradiation device can also be adapted by the change or the like of the shape and position of the cam 206 shown in FIG. 12 so that the traveling rotation and revolution of the rear wheel units 12R are restrained in a case in which the rear wheel-side pedal 500 and the front wheel-side pedal 501 are set to the lower positions and the revolution of the rear wheel units 12R is restrained in a case in which the rear wheel-side pedal 500 and the front wheel-side pedal 501 are set to the upper positions.

In addition, first and second locking means, which are basically the same as those shown in FIG. 7, may be connected to the brake shaft 402. According to this structure, the revolution of the rear wheel units 12R is restrained in a case in which the rear wheel-side pedal 500 and the front wheel-side pedal 501 are set to the lower positions, the traveling rotation of the rear wheel units 12R is restrained in a case in which the rear wheel-side pedal 500 and the front wheel-side pedal 501 are set to the upper positions, and the revolution and traveling rotation of the rear wheel units 12R can be performed in a case in which the rear wheel-side pedal 500 and the front wheel-side pedal 501 are set to the middle positions.

Further, for example, on the contrary to the example, the radiation-irradiation device can also be adapted by the change or the like of the position of the cam 106 shown in FIG. 7 so that the traveling rotation of the rear wheel units 12R is restrained in a case in which the rear wheel-side pedal 500 and the front wheel-side pedal 501 are set to the lower positions and the revolution of the rear wheel units 12R is restrained in a case in which the rear wheel-side pedal 500 and the front wheel-side pedal 501 are set to the upper positions.

As described above, in this embodiment, the rear wheel-side pedal 500 and the front wheel-side pedal 501 are disposed on the rear side and the front side of the middle position of the base 11 in the above-mentioned forward and rearward directions (±y directions), respectively. That is, in more detail, the rear wheel-side pedal 500 is disposed on the rear side of the rear end face 11a of the base 11 and the front wheel-side pedal 501 is disposed on the front side of the front end face 11b of the base 11.

The following effects can be obtained from this structure. That is, in a case in which an operator transports the radiation-irradiation device from the rear side of the base 11 while holding the handle 26 (see FIG. 1), a brake operation can be performed by the rear wheel-side pedal 500 as in the other embodiments. Further, in a case in which an operator desires that the position of the radiation-irradiation device is finely adjusted for imaging after transporting the radiation-irradiation device to a position close to the bed 3 (see FIG. 2) on which a subject H lies, the operator may also move to the front side of the base 11 and move the base 11. In a case in which the operator moves the base 11 under such a situation, the operator can perform a brake operation with the front wheel-side pedal 501.

Particularly, since the rear wheel-side pedal 500 and the front wheel-side pedal 501 are adapted to interlock with each other in this embodiment, the operator can easily grasp the current states of the first and second locking means by confirming the position of the front wheel-side pedal 501 in a case in which the operator moves to the front side from the rear side of the base 11 as described above. The same applies to a case in which the operator moves to the rear side from the front side of the base 11.

The rear wheel-side pedal 500 may be disposed on the left and/or right end face at a position close to the rear end face 11a of the base 11 other than a structure in which the rear wheel-side pedal 500 is disposed on the rear side of the rear end face 11a of the base 11. Likewise, the front wheel-side pedal 501 may also be disposed on the left and/or right end face at a position close to the front end face 11b of the base 11 other than a structure in which the front wheel-side pedal 501 is disposed on the front side of the front end face 11b of the base 11. However, it is preferable to dispose the rear wheel-side pedal 500 and the front wheel-side pedal 501 as in this embodiment to avoid the interference between the radiation-irradiation device and obstacles and the like that are positioned around the radiation-irradiation device during the transport of the radiation-irradiation device.

Ninth Embodiment

Figure 23:
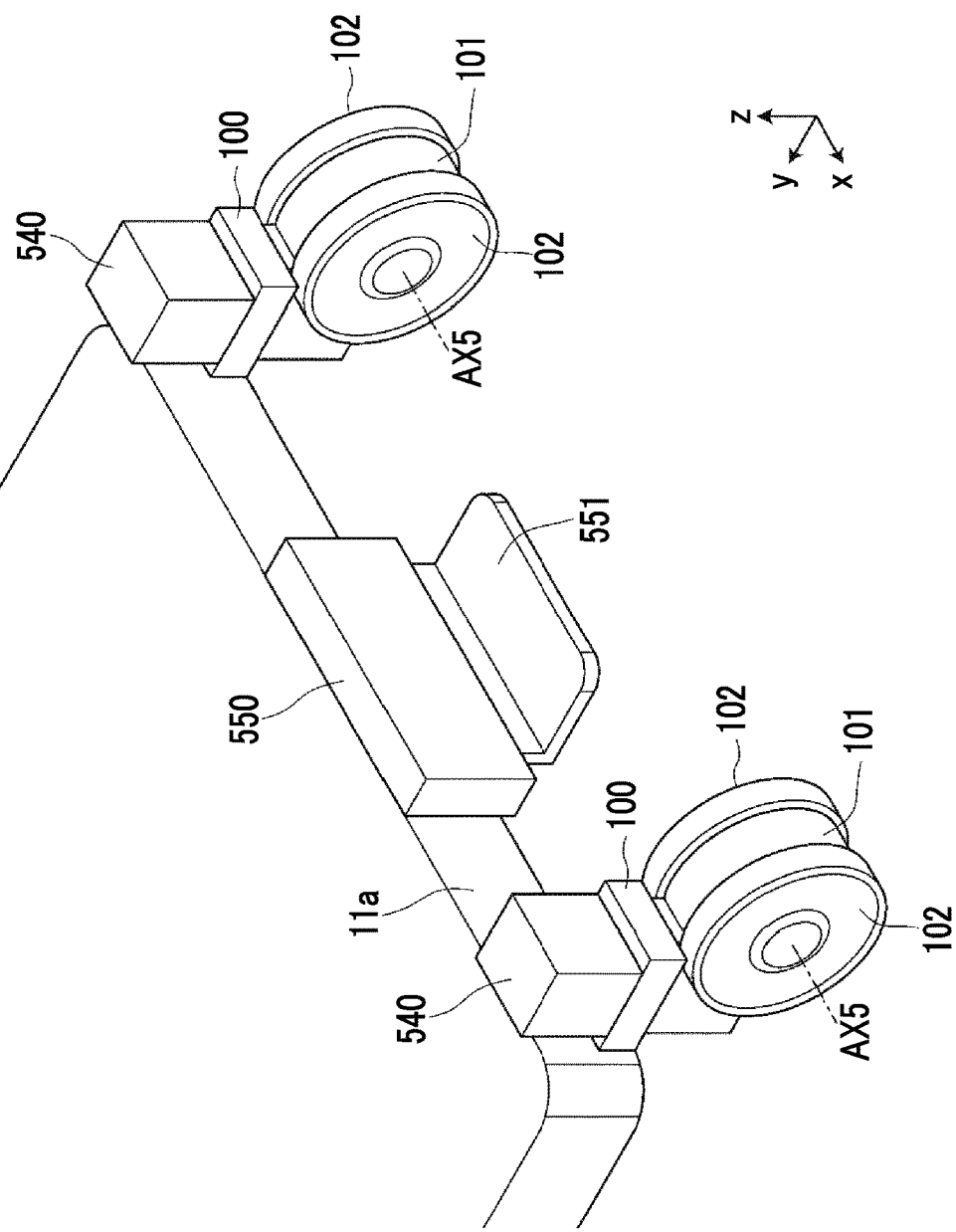
FIG. 23 is a perspective view showing peripheral portions of rear wheels of a radiation-irradiation device according to a ninth embodiment of the invention.

Next, a radiation-irradiation device according to a ninth embodiment of the invention will be described with reference to FIG. 23. FIG. 23 is a perspective view showing peripheral portions of rear wheels of the radiation-irradiation device according to the ninth embodiment of the invention. As shown in FIG. 23, actuators 540, which rotationally drive the shafts 108 (see FIG. 12) in a normal direction and a reverse direction, are provided in this embodiment to operate the first and second locking means shown in, for example, FIG. 12. Further, a control box 550, which receives an actuator control circuit for controlling the operations of the actuators 540 and a pressure sensor (all of them are not shown), is fixed to the rear end face 11a of the base 11. A pedal 551 serving as an operating piece, which is used to operate the first and second locking means, is mounted on the lower portion of the control box 550.

Furthermore, although not shown, a control box, which receives the same pressure sensor as the pressure sensor, is also fixed to the front end face 11b (see FIG. 22) of the base 11 and the same pedal as the pedal 551 is mounted on the lower portion of the control box. The pressure sensors are electrically connected to the actuator control circuit that is received in the control box 550.

The base portion of the pedal 551 is connected to the pressure sensor that is received in the control box 550. Accordingly, the pressure sensor detects a pedal effort that is applied to the pedal 551 and is included in one pedal effort range among a first pedal effort range that is smaller than a certain threshold value P1, a second pedal effort range that is the range of the threshold value P1 and a threshold value P2 (P1<P2), and a third pedal effort range that is larger than the threshold value P2. In a case in which the detected pedal effort is included in the first pedal effort range, the second pedal effort range, or the third pedal effort range, the actuator control circuit drives the actuator 540 into a state in which the revolution of the rear wheel units 12R is restrained, a state in which the revolution and the traveling rotation of the rear wheel units 12R are restrained, or a state in which the revolution and the traveling rotation of the rear wheel units 12R can be performed. The fact that the actuator 540 is driven on the basis of the pedal effort of the pedal 551 as described above also applies to the pedal that is provided on the front end face 11b of the base 11.

In this embodiment, the pedal 551 provided on the rear end face 11a of the base 11 does not interlock with the pedal provided on the front end face 11b of the base 11. However, in a case in which the pedal is moved so as to be selectively set to any one of the three positions and the states of the first and second locking means are controlled according to each pedal position instead of the detection of a pedal effort in the three range performed as described above, the two pedals can also be made to interlock with each other.

Further, since the states of the first and second locking means are adapted to be switched by the drive of the actuators 540 in this embodiment, a correspondence relationship between the state of the locking means and a pedal effort can be appropriately changed by only the change of the electrical configuration. For example, in a case in which the detected pedal effort is included in the first pedal effort range, the second pedal effort range, or the third pedal effort range, the actuator 540 can also be driven into a state in which the revolution and traveling rotation of the rear wheel units 12R are restrained, a state in which the revolution of the rear wheel units 12R is restrained, or a state in which the revolution and the traveling rotation of the rear wheel units 12R can be performed.

Tenth Embodiment

Figure 24:
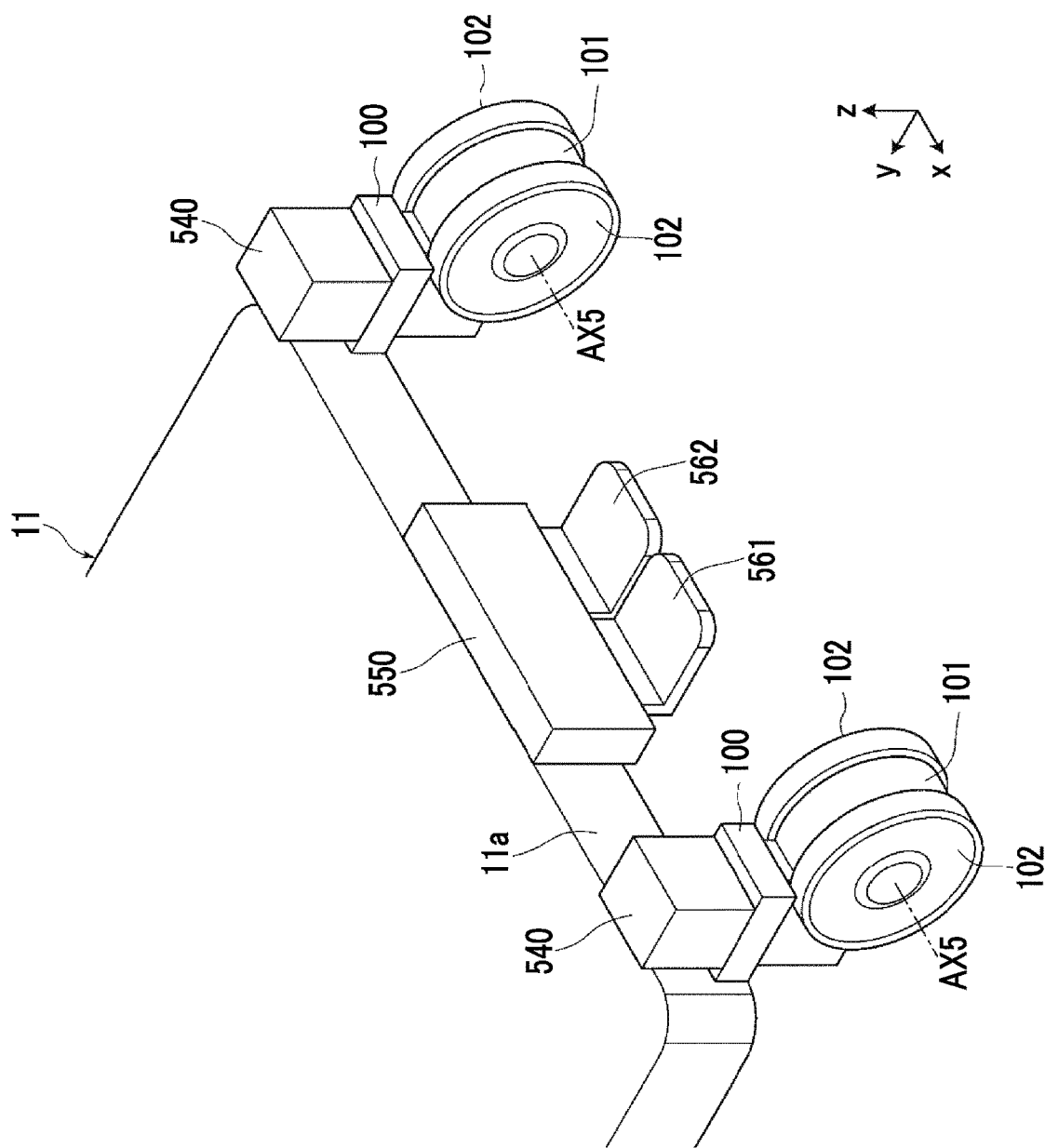
FIG. 24 is a perspective view showing peripheral portions of rear wheels of a radiation-irradiation device according to a tenth embodiment of the invention.

Next, a radiation-irradiation device according to a tenth embodiment of the invention will be described with reference to FIG. 24. FIG. 24 is a perspective view showing peripheral portions of rear wheels of the radiation-irradiation device according to the tenth embodiment of the invention. As shown in FIG. 24, the same actuators 540 and the control box 550 as those of the ninth embodiment shown in FIG. 23 are provided in this embodiment. Further, in this embodiment, a first pedal 561 and a second pedal 562 serving as an operating piece are provided instead of one pedal 551 shown in FIG. 23. In a case in which each of the first and second pedals 561 and 562 is stepped on with, for example, a foot, each of the first and second pedals 561 and 562 oscillates about an oscillation axis (not shown) extending in the x direction in the control box 550.

In more detail, the first pedal 561 selectively takes any one of a normal position that is shown in FIG. 24 and a stepping position where an operator steps on the first pedal 561 to allow the first pedal 561 to oscillate so that the rear portion of the first pedal 561 in FIG. 24 is lowered. The second pedal 562 selectively takes any one of a normal position that is shown in FIG. 24, a first stepping position where an operator steps on the second pedal 562 to allow the second pedal 562 to oscillate so that the rear portion of the second pedal 562 in FIG. 24 is lowered, and a second stepping position where an operator further steps on the second pedal 562 from the first stepping position so that the rear portion is further lowered. Further, if an operator steps on the second pedal 562 in a case in which the first pedal 561 is positioned at the stepping position, the first pedal 561 returns to the normal position. On the contrary, if an operator steps on the first pedal 561 in a case in which the second pedal 561 is positioned at the first or second stepping position, the second pedal 562 returns to the normal position.

The actuator control circuit controls the drive of the actuators 540 according to the positions of the first and second pedals 561 and 562 that are detected by position sensors. That is, the actuator control circuit drives the actuators 540 into a state in which the revolution of the rear wheel units 12R is restrained, in a case in which the first pedal 561 is positioned at the stepping position (in this case, the second pedal 562 returns to the normal position). Further, the actuator control circuit drives the actuators 540 into a state in which the revolution and traveling rotation of the rear wheel units 12R are restrained, in a case in which the second pedal 562 is positioned at the first stepping position (in this case, the first pedal 561 returns to the normal position). Furthermore, the actuator control circuit drives the actuators 540 into a state in which the revolution and traveling rotation of the rear wheel units 12R can be performed, in a case in which the second pedal 562 is positioned at the second stepping position (in this case, the first pedal 561 returns to the normal position).

Even in this embodiment, the same two pedals as the first and second pedals 561 and 562 and the same control box as the control box 550 can be provided on the front end face 11b (see FIG. 22) of the base 11 and the actuators 540 can be driven in the same manner as described above by the operation of these pedals. In the case of this structure, the first pedal 561 can be made to interlock with the same pedal provided on the front end face 11b of the base 11 and the second pedal 562 can be made to interlock with the same pedal provided on the front end face 11b of the base 11. An interlock between these pedals can be realized with a publicly known mechanism.

Figure 25:
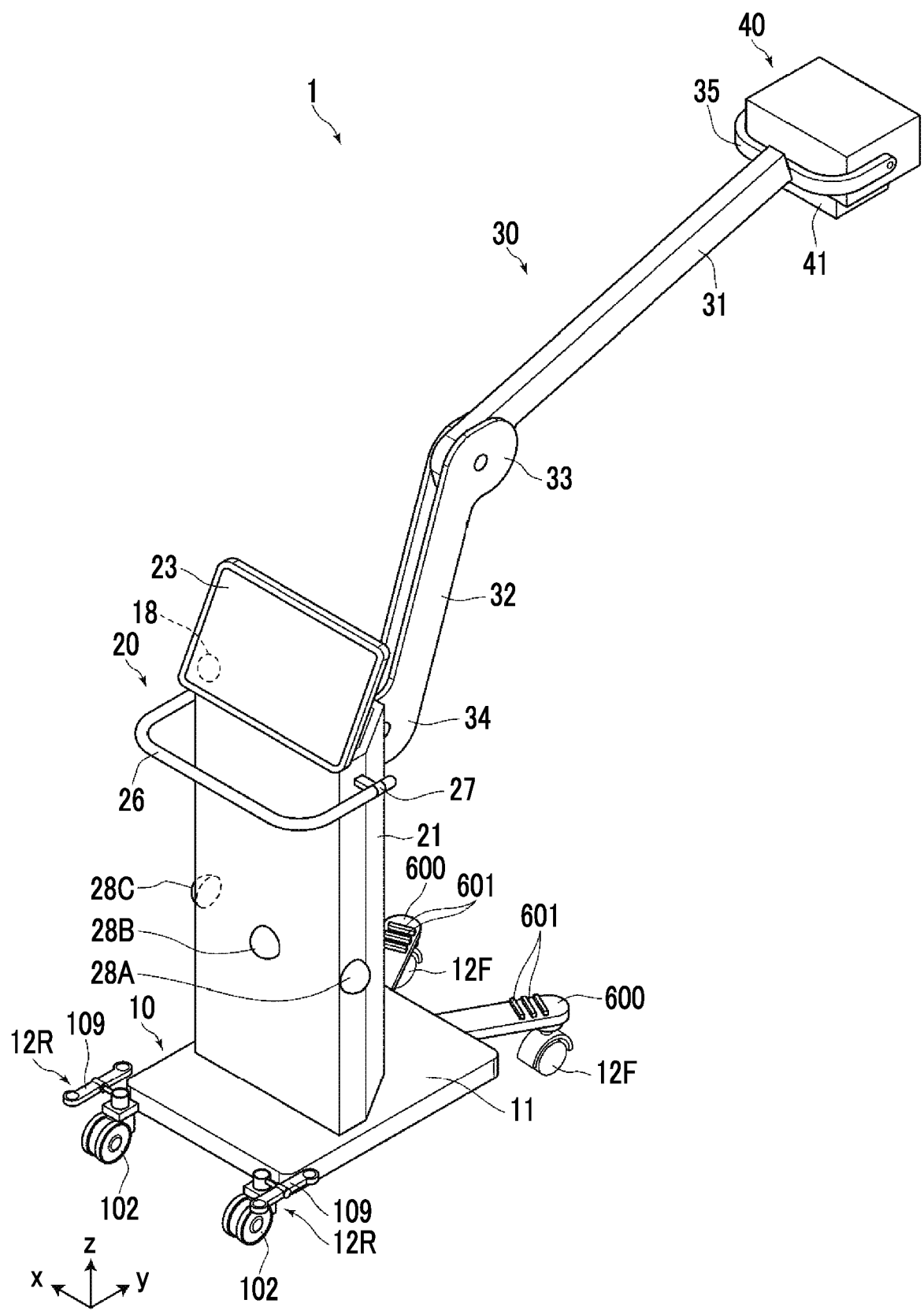
FIG. 25 is a perspective view showing an example of a radiation-irradiation device to which a structure for restraining the movement of a base is applied.

Incidentally, as described above, an operator may also move to the front side of the base 11 and move the base 11 in a case in which the operator desires that the position of the radiation-irradiation device is finely adjusted. Under such a situation, the operator desires that the movement of the base 11 is simply suppressed for a short time in addition to the operation of the first and second locking means. FIG. 25 is a perspective view showing an example of a radiation-irradiation device having a structure that can respond to such a request. In the structure shown in FIG. 25, two front wheel holding members 600, which extend from the base 11 and hold the front wheel units 12F, are provided and non-slip portions 601 are formed on the upper surface of each front wheel holding member 600. Each non-slip portion 601 is formed of, for example, a plurality of thin prismatic members that are installed side by side. The front wheel holding members 600 and the non-slip portions 601 can be made of, for example, a synthetic resin. Accordingly, an operator can simply restrain the movement of the base 11 by putting, for example, the bottom of the shoe of one foot on these non-slip portions 601 and pressing the front wheel holding member 600.

Further, two front wheel units 12F and two rear wheel units 12R have been provided in the respective embodiments having been described above, but the numbers of the front and rear wheel units 12F and 12R to be installed are not limited thereto. For example, one front wheel unit 12F and two rear wheel units 12R may be provided.

Further, the radiation-irradiation device of the above-mentioned embodiment has been made to travel by an operator's force. However, the radiation-irradiation device of the invention may include a power source, such as a motor, and may be adapted to automatically travel. Alternatively, the radiation-irradiation device of the invention may be adapted to travel by an operator's force while a drive force generated from a power source assists an operator.

What is claimed is:

1. A radiation-irradiation device comprising:
   a base;
   an arm unit that is mounted on the base and is capable of elongating and contracting in a plan view;
   a radiation source that is mounted on the arm unit; and
   a wheel unit that is mounted on the base and allows the base to travel on a device-placement surface,
   wherein the wheel unit includes a front wheel unit and at least two rear wheel units that are positioned on a rear side of the front wheel unit in a case in which an elongation direction of the arm unit in the plan view is forward and are away from each other in a direction crossing the elongation direction of the arm unit,
   wherein each of the rear wheel units includes a wheel that performs traveling rotation for the traveling, and a traveling direction-changing part that changes a direction of the traveling, and
   wherein each of the rear wheel units further includes first locking section for restraining the traveling rotation of the wheel, and second locking section capable of operating independently of the first locking section and restraining an operation of the traveling direction-changing part.

2. The radiation-irradiation device according to claim 1, wherein the rear wheel unit is formed of a revolving caster, and the traveling direction-changing part is a revolving part of the revolving caster.

3. The radiation-irradiation device according to claim 1, wherein the rear wheel unit is formed of OMNI WHEEL, and the traveling direction-changing part is a roller that is mounted on a wheel body of the OMNI WHEEL.

4. The radiation-irradiation device according to claim 1, further comprising:
   an operating portion that includes operating pieces receiving an operating force applied from the outside and operates the first and second locking section,
   wherein the operating portion is provided with a plurality of the operating pieces, and
   at least one of the plurality of operating pieces is disposed on each of front and rear sides of a middle position of the base in a forward direction and a rearward direction.

5. The radiation-irradiation device according to claim 4, wherein:
   the operating piece is disposed on a rear side of a rear end of the base; and
   the operating piece is disposed on a front side of a front end of the base.

6. The radiation-irradiation device according to claim 4, wherein the plurality of operating pieces interlock with each other.

7. The radiation-irradiation device according to claim 1, wherein each of the rear wheel units is provided with a locking-operating part for one wheel that exclusively takes a first state in which at least the first locking section is operated and a second state in which the second locking section is operated.

8. The radiation-irradiation device according to claim 1, wherein each of the rear wheel units is provided with a locking-operating part for one wheel that exclusively takes a first state in which at least the first and second locking section are operated and a second state in which the second locking section is operated.

9. The radiation-irradiation device according to claim 7, wherein the locking-operating part for one wheel includes a seesaw-like operating piece oscillating about one fulcrum, takes the first state in a case in which the operating piece oscillates about the fulcrum in one direction, takes the second state in a case in which the operating piece oscillates about the fulcrum in the other direction, and takes a third state in which the first and second locking section are not operated in a case in which the operating piece does not oscillate not only in one direction but also in the other direction.

10. The radiation-irradiation device according to claim 1, further comprising:
    a locking-operating part for a plurality of wheels that operates the respective second locking section of the rear wheel units in parallel.

11. The radiation-irradiation device according to claim 1, wherein two front wheel units are provided and two rear wheel units are provided.

12. The radiation-irradiation device according to claim 1, wherein one front wheel unit is provided and two rear wheel units are provided.

* * * * *